US010780275B2

(12) United States Patent
Robinson et al.

(10) Patent No.: US 10,780,275 B2
(45) Date of Patent: Sep. 22, 2020

(54) IMPLANTABLE NEURO-STIMULATION DEVICE

(71) Applicant: Mudjala Medical Pty Limited, Bronte (AU)

(72) Inventors: David Robinson, Bronte (AU); Ernest Mantes, The Colony, TX (US); Tracy Cameron, Toronto (CA)

(73) Assignee: Mudjala Medical Pty Limited, Bronte (AU)

( * ) Notice: Subject to any disclaimer, the term of this patent is extended or adjusted under 35 U.S.C. 154(b) by 237 days.

(21) Appl. No.: 15/786,149

(22) Filed: Oct. 17, 2017

(65) Prior Publication Data
US 2018/0117332 A1    May 3, 2018

Related U.S. Application Data

(63) Continuation-in-part of application No. PCT/US2016/027570, filed on Apr. 14, 2016.

(30) Foreign Application Priority Data

Jun. 27, 2015    (AU) ................................. 2015902501

(51) Int. Cl.
*A61N 1/36*    (2006.01)
*A61N 1/05*    (2006.01)

(52) U.S. Cl.
CPC ....... *A61N 1/36071* (2013.01); *A61N 1/0551* (2013.01); *A61N 1/0556* (2013.01);
(Continued)

(58) Field of Classification Search
CPC .............. A61N 1/36071; A61N 1/0551; A61N 1/36067; A61N 1/0504; A61N 1/36082; A61N 1/36128
See application file for complete search history.

(56) References Cited

U.S. PATENT DOCUMENTS 5,074,313 A * 12/1991 Dahl ..................... A61B 5/042
607/119
7,493,175 B2    2/2009 Cates et al.
(Continued)

FOREIGN PATENT DOCUMENTS

AU       2012201634 B2    7/2013
WO    WO-2016168485 A1    10/2016

OTHER PUBLICATIONS

International Search Report and Written Opinion dated Sep. 2, 2016 for International PCT Patent Application No. US-2016/027570.
(Continued)

*Primary Examiner* — Lindsey G Wehrheim
(74) *Attorney, Agent, or Firm* — Wilson Sonsini Goodrich & Rosati

(57) ABSTRACT

An implantable electrical stimulation device includes an electrically conductive electrode structure configured for coupling with a pulse generator device and transmitting an electrical signal configured to generate a desirable electric field around a target tissue. The electrode structure includes a porous substrate constructed of a bio-compatible and bio-survivable material having a structure that mimics extracellular matrix embedding. The porous substrate supports an electrically conductive electrode element. The implantable device may further include a pulse generator also embedded, enmeshed, and supported within the porous substrate.

21 Claims, 24 Drawing Sheets

(52) U.S. Cl.
CPC ....... *A61N 1/3615* (2013.01); *A61N 1/36057* (2013.01); *A61N 1/36067* (2013.01); *A61N 1/36139* (2013.01); *A61N 1/36146* (2013.01); *A61N 1/36178* (2013.01); *A61N 1/0504* (2013.01); *A61N 1/0526* (2013.01); *A61N 1/0558* (2013.01); *A61N 1/36082* (2013.01); *A61N 1/36128* (2013.01)

(56) References Cited

U.S. PATENT DOCUMENTS

| | | |
|---|---|---|
| 8,060,219 B2 | 11/2011 | Ross et al. |
| 8,239,044 B1 | 8/2012 | Tranchina |
| 2006/0204738 A1 | 9/2006 | Dubrow et al. |
| 2007/0060815 A1 | 3/2007 | Martin et al. |
| 2009/0105796 A1 | 4/2009 | Atanasoska et al. |
| 2009/0171406 A1 | 7/2009 | Foley et al. |
| 2010/0049289 A1 | 2/2010 | Lund et al. |
| 2010/0185268 A1 | 7/2010 | Fowler et al. |
| 2011/0172736 A1 | 7/2011 | Gefen et al. |
| 2012/0043011 A1 | 2/2012 | Claude et al. |
| 2012/0310316 A1 | 12/2012 | Janik et al. |
| 2013/0006320 A1 | 1/2013 | Hintz et al. |
| 2014/0200626 A1 | 7/2014 | Campbell et al. |
| 2014/0343673 A1 | 11/2014 | Matheny |
| 2015/0297798 A1 | 10/2015 | Badylak et al. |

OTHER PUBLICATIONS

EP16780758.5 Extended Search Report dated Dec. 11, 2018.

\* cited by examiner

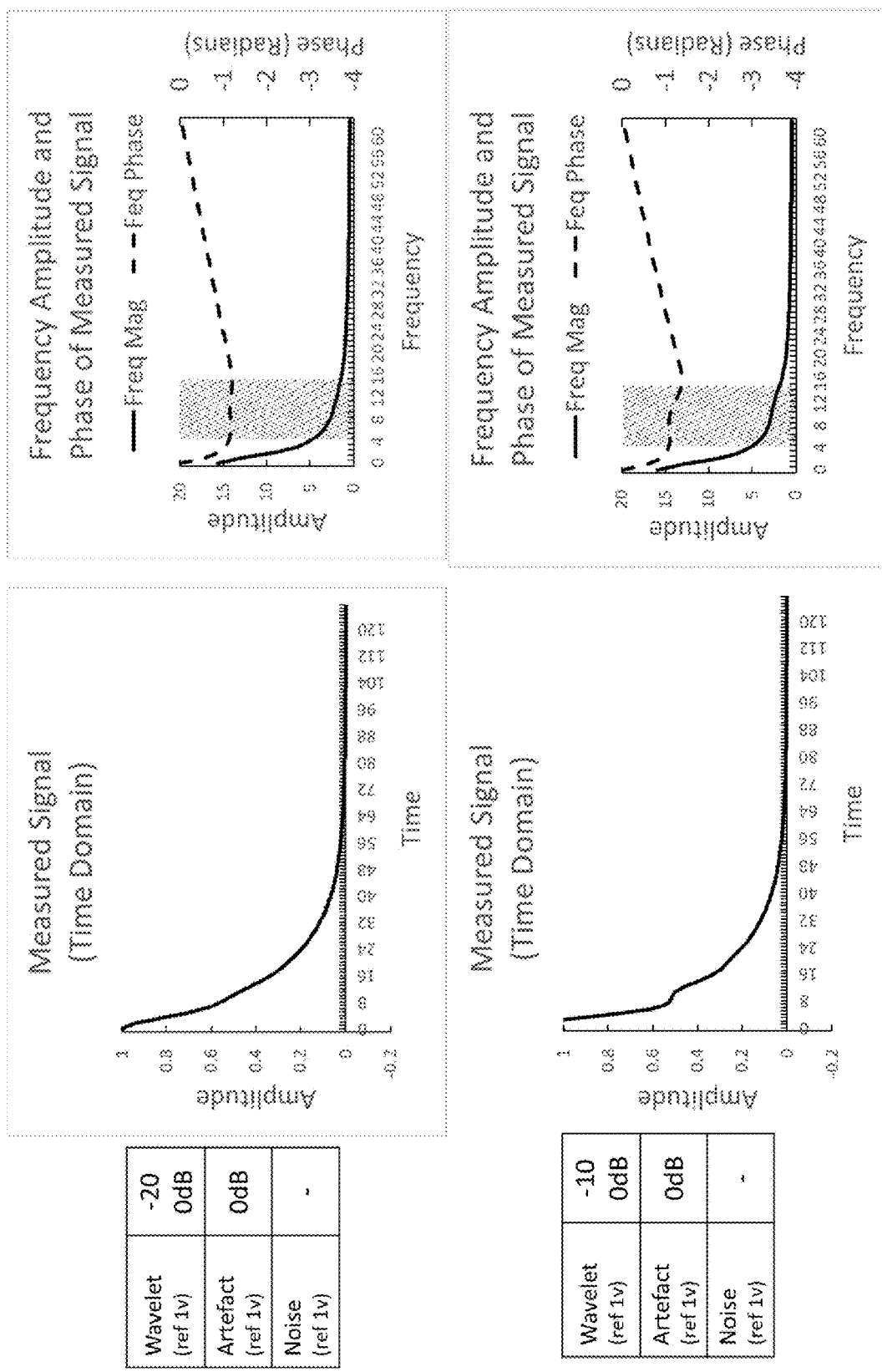

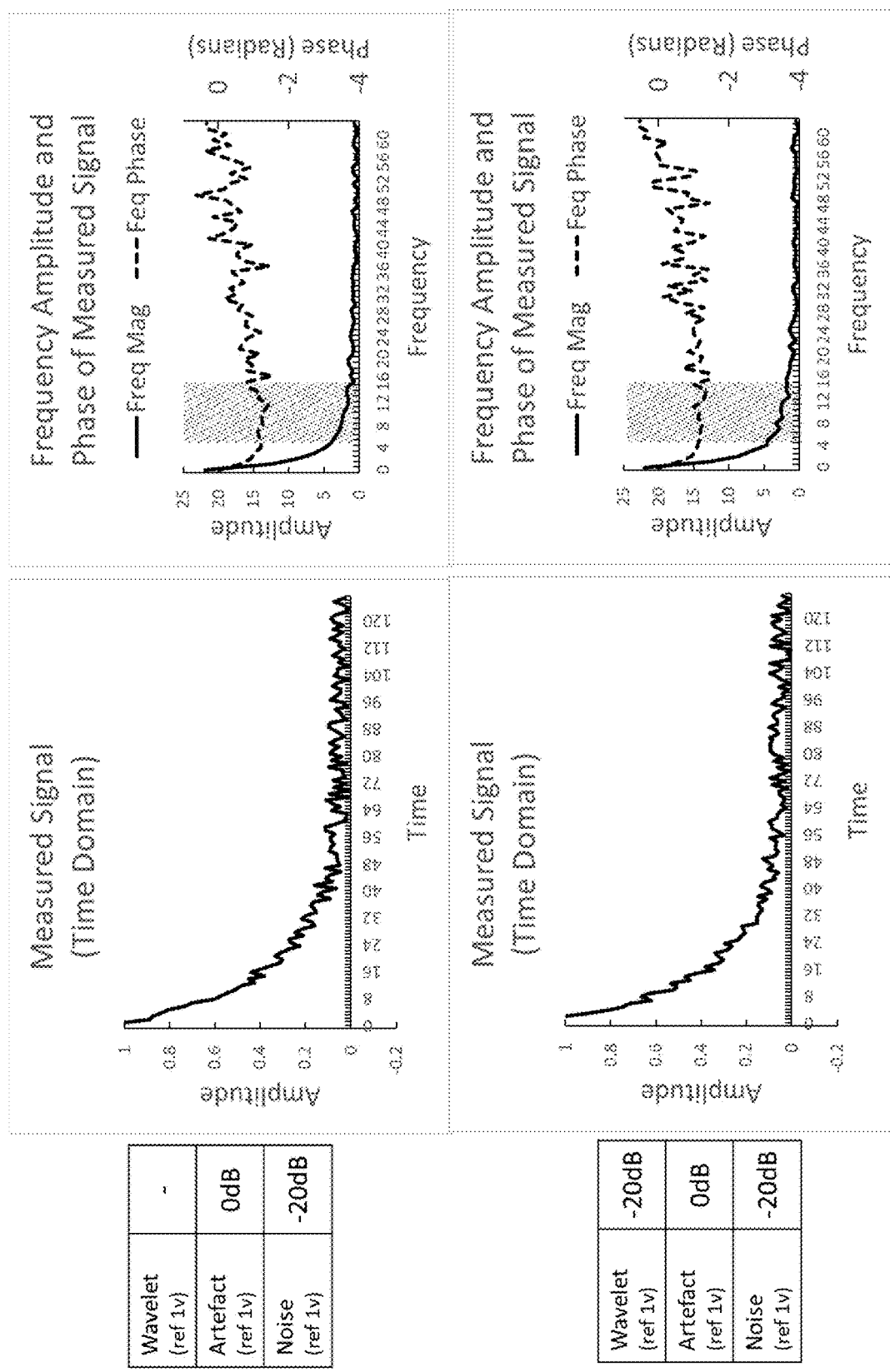

IMPLANTABLE NEURO-STIMULATION DEVICE

CROSS-REFERENCE TO RELATED APPLICATIONS

The present application is continuation-in-part of PCT/US2016/027570, filed on Apr. 14, 2016, entitled "An Implantable Neurostimulation Device," which claims the benefit of Australian Provisional Patent Application No. 201590902501, filed Jun. 27, 2015, entitled "A Method and Apparatus for Providing Paraesthesia Pain Relief by Neuromodulation," and of Australian Provisional Patent Application No. 2015901380 filed Apr. 17, 2015, entitled "A System and Method of Manufacture for a Peripheral Nervous System Neurostimulation," the full disclosures of which are incorporated herein by reference.

BACKGROUND OF THE INVENTION

The present disclosure relates to the field of neuromodulation or neuro-stimulation for therapeutic benefit, and in particular to: a structure and method of manufacture of an implantable neuro-stimulation lead in a porous substrate; an implantable peripheral neuromodulation system and method of manufacturing; a method and apparatus for providing complex therapeutic outcomes; and a method and apparatus for neural circuit processing.

Neuromodulation or neuro-stimulation is a therapeutic activation of parts of the nervous system by delivering electrical stimulation using microelectrodes. The use of neuro-stimulation for therapeutic benefit has a long history. The use of neuro-stimulation to provide relief of chronic intractable pain by selective stimulation of nerves in the spinal cord has been practiced since Melzack and Wall proposed the Gate Control Theory in 1965. The Gate Control Theory proposes that nerves carrying painful stimuli (classified as "C" fibers) and nerves carrying non-painful stimuli such as touch, pressure, and vibratory sensations (classified as afferent "A-β" fibers) both terminate in the dorsal horn or "gate" of the spinal cord where they interact. Theory further proposes that when the afferent A-β fibers were activated it would have the effect of "closing the gate" on the C fibers, and thereby reducing or alleviating the sensation of pain. Vallejo, Bradley, and Kapural, (*Spinal Cord Stimulation in Chronic Pain: Mode of Action* Spine: 15 Jul. 2017—Volume 42—Issue—p S53-S60) have further concluded that "the activation of A-beta fibers to induce paresthesia also involves neurotransmitter release via segmental and supraspinal pathways." It is widely believed that the release of neurotransmitters as a result of neuro stimulation is a key element of many neuro stimulation therapies.

The term "neuromodulation" is defined by the International Neuromodulation Society as "the alteration of nerve activity through the delivery of electrical stimulation or chemical agents to targeted sites of the body." Electrical neuromodulation therapies can therefore be defined as any alteration of nerve activity through the delivery of electrical stimulation which delivers a therapeutic benefit to the patient. Electrical neuromodulation therapies may be delivered externally, using an electrode placed on the skin over/near the target nerve, or internally, using an implanted electrode placed subcutaneously near the target nerve or nerves or directly on the target nerve, which is connected to an Implantable Pulse Generator (IPG). Implantable neuromodulation devices came into modern usage in the 1980's and the techniques and applications of this technology have continued to develop and expand.

Spinal cord stimulation (SCS) is a form of neuromodulation therapy in use since the 1980's. Its principal use is as a reversible, non-pharmacological therapy for chronic pain management that delivers mild electrical pulses to the spinal cord. Another neuromodulation treatment developed in the 1980's is deep brain stimulation (DBS), which may be used to help limit symptoms of movement disorder in Parkinson's disease, dystonia, or essential tremor. Since elements of the nervous system can be broadly classified as belonging to either the central nervous system or peripheral nervous system, electrical neuromodulation therapies may also be classified as Central Nervous System Stimulation (CNSS) and Peripheral Nervous System Stimulation (PNSS). Spinal Cord Stimulation (SCS) and Deep Brain Stimulation (DBS) (the oldest and most common electrical neuromodulation therapies in use today) are both examples of CNSS. Other known applications of neuromodulation therapy include occipital nerve stimulation (ONS), peripheral nerve stimulation (PNS), vagus nerve stimulation (VNS), sacral nerve stimulation (SNS), which are examples of PNSS.

SUMMARY OF THE INVENTION

In accordance with one aspect of the present invention, an implantable electrical stimulation device comprises a porous substrate constructed of a bio-compatible and bio-survivable material. At least one electrically conductive electrode is embedded in the porous substrate and configured for coupling with a pulse generator device. The pulse generator device is configured for transmitting an electrical signal from the pulse generator device to generate an electric field around a target tissue, and the porous substrate is further configured to fully support the at least one electrically conductive electrode to provide structural integrity to the implantable electrical stimulation device.

In specific embodiments, the porous substrate may mimic extracellular matrix.

In specific embodiments, the porous substrate has a pore size selected to control tissue in growth. For example, the pore size may selected to allow only superficial cellular ingrowth. Alternatively, the pore size may selected to allow only cellular ingrowth in selected areas the substrate. Exemplary pore sizes are in a range from 2 μm to 10 μm.

In specific embodiments, the porous substrate is constructed of non-woven fibers. For example, the non-woven fibers may be polymeric fibers. Exemplary polymeric fibers may be selected from a group consisting of polyurethane (thermoplastic and thermoset), polyethylene terephthalate, polyether ether ketone, polytetrafluoroethylene and polymethyl-methacrylate.

In specific embodiments, the porous substrate may support the one or more conductive electrodes in such a way that part of one or more electrodes and the surrounding porous substrate can be removed without compromising the integrity of the overall structure, for example a blend of 60% polyurethane and 40% polyethylene terephthalate.

In specific embodiments, the porous substrate comprises two or more materials, at least one of which may be selected to facilitate bonding with another part of the membrane or another membrane by the application of heat, pressure, bonding agent or other means.

In specific embodiments, at least one electrically non-conductive inclusion that is impervious to electrolyte penetration disposed on or within the porous substrate.

In specific embodiments, an electrically conductive field shaping element may be embedded within the porous substrate and configured for shaping the electric field generated by the electrically conductive electrode.

In specific embodiments, the implantable electrical stimulation may further comprise an electrically insulated lead embedded within the porous substrate and configured for shaping the electric field generated by the electrically conductive electrode.

In specific embodiments, the implantable electrical stimulation may further comprise an electrically conductive inclusion configured to function as an electrical connecting element disposed within the porous substrate.

In specific embodiments, the implantable electrical stimulation may further comprise a biocompatible and resorbable inclusion configured to function as a structural element disposed within the porous substrate In specific embodiments, the implantable electrical stimulation may further comprise a biocompatible and non-resorbable inclusion configured to function as a structural element disposed within the porous substrate.

In specific embodiments, the porous substrate may be substantially free from structural element disposed therein.

In specific embodiments, the implantable electrical stimulation may further comprise a biocompatible inclusion configured to function as an anchor structure at least partly disposed within the porous substrate.

In specific embodiments, the implantable electrical stimulation may further comprise a biocompatible inclusion in the form of barbed structures configured to function as an anchor structure at least partly disposed within the porous substrate.

In specific embodiments, a pore size of at least one region of at least one of the porous substrate is different than a pore size in another region of the porous substrate.

In specific embodiments, at least one selected region of the porous substrate is impervious to electrolyte penetration.

In specific embodiments, least one selected region of the porous substrate is coated with an electrically non-conductive material for the purpose of shaping the electric field.

In specific embodiments, at least one selected region of the porous substrate is coated with an electrically non-conductive material for the purpose of modifying surface properties of the lead assembly.

In specific embodiments, the implantable electrical stimulation may further comprise a second porous substrate constructed around at least some of the lead structure to allow retraction and removal of the lead structure post-implantation.

In specific embodiments, the lead assembly may be in the form and structure of one of a patch lead, paddle lead, cuff lead, helical lead, transvenous lead, conformal lead and catheter lead.

In specific embodiments, the lead assembly may be configured for generating an electric field around a target nerve.

In specific embodiments, the implantable electrical stimulation may further comprise a pulse generator circuit embedded within the porous substrate and electrically connected to the at least one electrically conductive electrode.

In specific embodiments, the pulse generator circuit may further include a power supply.

In specific embodiments, at least one selected region of the porous substrate may be coated with an electrically non-conductive material for the purpose of modifying surface properties of the lead assembly.

In specific embodiments, the implantable electrical stimulation may further comprise a second porous substrate constructed around at least some of the lead structure to allow retraction and removal of the lead structure post-implantation.

In specific embodiments, the lead assembly may be in the form and structure of one of a patch lead, paddle lead, cuff lead, helical lead, transvenous lead, conformal lead and catheter lead.

In specific embodiments, the lead assembly is configured for generating an electric field around a target nerve.

In specific embodiments, the implantable electrical stimulation may further comprise a pulse generator circuit embedded within the porous substrate and electrically connected to the at least one electrically conductive electrode.

In specific embodiments, the pulse generator circuit further includes a power supply.

Other aspects of the present invention are set forth in the following numbered clauses:

Clause 1: An implantable electrical stimulation device comprising at least one electrically conductive electrode configured for coupling with a pulse generator device and transmitting an electrical signal configured to generate a desirable electric field around a target tissue; and a porous substrate constructed of a bio-compatible and bio-survivable material having a structure that mimics extracellular matrix embedding and supporting the electrically conductive electrode.

Clause 2: The implantable electrical stimulation device of clause 1, wherein the porous substrate is constructed of non-woven fibers.

Clause 3: The implantable electrical stimulation device of clause 1, further comprising at least one electrically non-conductive inclusion that is impervious to electrolyte penetration disposed within the porous substrate.

Clause 4: The implantable electrical stimulation device of clause 1, further comprising at least one intermediate non-porous layer disposed within the porous substrate.

Clause 5: The implantable electrical stimulation device of clause 1, further comprising an electrically conductive field shaping element embedded within the porous substrate and configured for shaping the electric field generated by the electrically conductive electrode.

Clause 6: The implantable electrical stimulation device of clause 1, further comprising an electrically insulated buried lead embedded within the porous substrate and configured for shaping the electric field generated by the electrically conductive electrode.

Clause 7: The implantable electrical stimulation device of clause 1, further comprising an electrically conductive inclusion configured to function as an electrical connecting element disposed within the porous substrate.

Clause 8: The implantable electrical stimulation device of clause 1, further comprising a biocompatible and resorbable inclusion configured to function as a structural element disposed within the porous substrate.

Clause 9: The implantable electrical stimulation device of clause 1, further comprising a biocompatible and non-resorbable inclusion configured to function as a structural element disposed within the porous substrate.

Clause 10: The implantable electrical stimulation device of clause 1, further comprising a biocompatible inclusion configured to function as an anchor structure at least partly disposed within the porous substrate.

Clause 11: The implantable electrical stimulation device of clause 1, further comprising a bio-compatible inclusion in the form of barbed structures configured to function as an anchor structure at least partly disposed within the porous substrate.

Clause 12: The implantable electrical stimulation device of clause 1, wherein a pore size of at least one selected region of at least one of the porous substrate is different than the rest of the porous substrate.

Clause 13: The implantable electrical stimulation device of clause 1, wherein at least one selected region of the porous substrate is impervious to electrolyte penetration.

Clause 14: The implantable electrical stimulation device of clause 1, wherein at least one selected region of the porous substrate is coated with an electrically non-conductive material for the purpose of shaping the electric field.

Clause 15: The implantable electrical stimulation device of clause 1, wherein at least one selected region of the porous substrate is coated with an electrically non-conductive material for the purpose of modifying surface properties of the lead assembly.

Clause 16: The implantable electrical stimulation device of clause 1, further comprising a second porous substrate constructed around at least some of the lead structure to allow retraction and removal of the lead structure post-implantation.

Clause 17: The implantable electrical stimulation device of clause 1, wherein the lead assembly is in the form and structure of one of a patch lead, paddle lead, cuff lead, helical lead, transvenous lead, conformal lead and catheter lead.

Clause 18: The implantable electrical stimulation device of clause 1, wherein the lead assembly is configured for generating an electric field around a target nerve.

Clause 19: The implantable electrical stimulation device of clause 1, further comprising a pulse generator circuit enclosed in an hermetical enclosure also embedded within the porous substrate and configured to generate an electrical signal.

Clause 20: The implantable electrical stimulation device of clause 19, wherein the pulse generator circuit further includes a power supply.

Clause 21: The implantable electrical stimulation device of clause 19, wherein the pulse generator circuit further includes an inductive coil configured to be energized by energy transmitted by an energy source that is external to the body.

Clause 22: The implantable electrical stimulation device of clause 21, wherein the external energy source is incorporated in a wearable accessory selected from the group consisting of a hat, a headband, a necklace, eyeglasses, sports headphone-like structure, a purse, a collar, and a Velcro patch.

Clause 23: A method of manufacturing an implantable neuro-stimulation device, comprising: forming a first part of a porous substrate over a mandrel of a suitable shape using a biocompatible and bio-survivable material, the porous substrate having a structure that mimics extracellular matrix; disposing at least one electrically conductive bio-compatible and bio-survivable element within the porous substrate, the at least one element configured for coupling with a pulse generator device and transmitting an electrical signal configured to generate a desirable electric field around a target nerve; and forming a final part of the porous substrate to embed, enmesh, and support the at least one electrically conductive element.

Clause 24: The method of clause 23, further comprising disposing at least one electrically conductive bio-compatible and bio-survivable element within the porous substrate configured to impart desirable mechanical and electrical properties to the lead assembly.

Clause 25: The method of clause 23, further comprising disposing at least one electrically non-conductive bio-compatible and bio-survivable element within the porous substrate configured to impart desirable mechanical and electrical properties to the lead assembly.

Clause 26: The method of clause 23, wherein forming the porous substrate comprises laying thin strands of fibers in a random pattern to form a non-woven material.

Clause 27: The method of clause 23, further comprising forming at least one intermediate non-porous layer within the porous substrate.

Clause 28: The method of clause 23, further comprising forming an electrically conductive field shaping element configured for shaping the electric field generated by the electrically conductive element within the porous substrate.

Clause 29: The method of clause 23, further comprising forming an electrically conductive inclusion configured to function as an electrical connecting element within the porous substrate.

Clause 30: The method of clause 23, further comprising forming an electrically non-conductive inclusion that is impervious to electrolyte penetration within the porous substrate.

Clause 31: The method of clause 23, further comprising forming a bio-compatible and resorbable inclusion configured to function as a structural element within the porous substrate.

Clause 32: The method of clause 23, further comprising forming a bio-compatible and non-resorbable inclusion configured to function as a structural element within the porous substrate.

Clause 33: The method of clause 23, further comprising forming a bio-compatible inclusion configured to function as an anchor structure at least partly within the porous substrate.

Clause 34: The method of clause 23, wherein forming the porous substrate comprises forming a pore size of at least one selected region of the porous substrate different than the rest of the porous substrate.

Clause 35: The method of clause 23, wherein forming the porous substrate comprises forming at least one selected region of the porous substrate impervious to electrolyte penetration.

Clause 36: The method of clause 23, wherein forming the porous substrate comprises coating at least one selected region of the porous substrate with an electrically non-conductive material for the purpose of shaping the electric field.

Clause 37: The method of clause 23, wherein forming the porous substrate comprises coating at least one selected region of the porous substrate with an electrically non-conductive material for the purpose of modifying surface properties of the lead assembly.

Clause 38: The method of clause 23, further comprising forming a second porous substrate around at least part of the electrically conductive element to allow retraction and removal thereof post-implantation.

Clause 39: The method of clause 23, wherein the lead assembly is manufactured in the form and structure of one of a patch lead, paddle lead, cuff lead, helical lead, transvenous lead, conformal lead and catheter lead.

Clause 40: The method of clause 23, further comprising disposing a pulse generator within the porous substrate and forming the final part of the porous substrate to embed, enmesh, and support the pulse generator within the porous substrate.

Clause 41: An implantable electrical stimulation device comprising at least one electrically conductive electrode configured for coupling with a pulse generator device and transmitting an electrical signal configured to generate a desirable electric field around a target tissue; a pulse generator circuit enclosed in an hermetical enclosure and configured to generate an electrical signal; a porous substrate constructed of a bio-compatible and bio-survivable material having a structure that mimics extracellular matrix embedding and supporting the electrically conductive electrode and the pulse generator circuit.

Clause 42: A method of manufacturing an implantable neuro-stimulation device, comprising: forming a first part of a porous substrate over a mandrel of a suitable shape using a biocompatible and bio-survivable material, the porous substrate having a structure that mimics extracellular matrix; disposing at least one electrically conductive bio-compatible and bio-survivable element within the porous substrate; disposing a pulse generator configured for coupling with the at least one electrically conductive bio-compatible and bio-survivable element, the pulse generator configured for generating an electrical signal to produce a desirable electric field around a target nerve; and forming a final part of the porous substrate to embed, enmesh, and support the pulse generator and the at least one electrically conductive element.

Clause 43: An implantable neural stimulation system comprising a lead assembly; and a pulse generator coupled to the lead assembly configured to generate two or more stimulation patterns each with a desired therapeutic outcome, and generate a further stimulation pattern with an enhanced therapeutic outcome by combining the two or more stimulation patterns.

Clause 44: The system of clause 43, wherein the pulse generator is configured to generate the further stimulation pattern by weighted addition of the two or more stimulation patterns.

Clause 45: The system of clause 43, wherein the pulse generator is configured to generate the further stimulation pattern by interleaving the two or more stimulation patterns.

Clause 46: The system of clause 43, wherein the pulse generator is configured to generate a first stimulation pattern intended to block transmission of sensations in a target nerve.

Clause 47: The system of clause 43, wherein the pulse generator is configured to generate a second stimulation pattern intended to activate fibers in a target nerve.

Clause 48: The system of clause 43, wherein the pulse generator is configured to independently modify parameters of each of the first and second stimulation patterns.

Clause 49: The system of clause 43, wherein the pulse generator is configured to generate the first stimulation pattern using at least one of constant voltage signal and constant current signal technique.

Clause 50: The system of clause 43, wherein the pulse generator is configured to generate a charge-balanced direct current (CBDC) stimulation pattern and a charge-balanced alternating current (CBAC) stimulation pattern, and generate a composite stimulation pattern with an enhanced therapeutic outcome by combining the CBDC and CBAC stimulation patterns.

Clause 51: The system of clause 43, wherein the pulse generator is configured to generate the stimulation patterns based on at least one of square, triangle, sinusoidal waveforms or some composite thereof.

Clause 52: The system of clause 43, wherein the pulse generator is configured to generate the stimulation patterns based on one of symmetrical and asymmetrical waveforms.

Clause 53: A method of neural stimulation for therapeutic outcomes comprising generating a first stimulation pattern with a first desired therapeutic outcome; generating a second stimulation pattern with a second desired therapeutic outcome; generating a third stimulation pattern with an enhanced therapeutic outcome by combining the first and second stimulation patterns; and transmitting the third stimulation pattern to an implanted lead assembly disposed proximate to a target nerve.

Clause 54: The method of clause 53, wherein generating the third stimulation pattern comprises performing a weighted addition of the first and second stimulation patterns.

Clause 55: The method of clause 53, wherein generating the third stimulation pattern comprises interleaving the first and second stimulation patterns.

Clause 56: The method of clause 53, further comprising independently adjusting parameters of each of the first and second stimulation patterns.

Clause 57: The method of clause 53, wherein generating the first, second, and third stimulation patterns comprises generating a charge-balanced direct current (CBDC) stimulation pattern and a charge-balanced alternating current (CBAC) stimulation pattern, and generating a composite stimulation pattern with an enhanced therapeutic outcome by combining the CBDC and CBAC stimulation patterns.

Clause 58: A method comprising stimulating an input element of a neural circuit with a stimulation waveform having a predetermined characteristic; measuring a response at an output element of the neural circuit; analyzing the measured response; and inferring a state of the neural circuit based on the measured response.

Clause 59: The method of clause 58, wherein inferring a state of the neural circuit comprises inferring information from the measured response for diagnostic purposes.

Clause 60: The method of clause 58, wherein inferring a state of the neural circuit comprises inferring information from the measured response for a purpose of determining a parameter of a beneficial therapy.

Clause 61: The method of clause 58, wherein inferring a state of the neural circuit comprises inferring information from the measured response for a purpose of determining a control parameter of a beneficial neuro-stimulation therapy.

Clause 62: The method of clause 58, wherein inferring a state of the neural circuit comprises inferring information from the measured response for a purpose of determining a control parameter of a beneficial drug delivery device.

Clause 63: The method of clause 58, wherein inferring a state of the neural circuit comprises inferring information about concentration of specific neurotransmitters between neurons in the neural circuit.

Clause 64: The method of clause 58, wherein stimulating the input element of a neural circuit comprises stimulating the input element of the neural circuit with a stimulation waveform that has an auto-correlation function with a single well-defined peak.

Clause 65: The method of clause 58, wherein stimulating the input element of a neural circuit comprises stimulating the input element of the neural circuit with a pseudo-random binary noise sequence signal.

Clause 66: The method of clause 65, wherein analyzing the measured response comprises cross-correlating the pseudo-random binary noise sequence signal at the input element with a measured response at the output element.

Clause 67: The method of clause 58, wherein stimulating the input element of a neural circuit comprises modulating the stimulation waveform between on and off states.

Clause 68: The method of clause 67, wherein analyzing the measured response comprises estimating a difference of a specific characteristic of the measured response when the stimulation waveform is on and when it is off.

Clause 69: The method of clause 67, wherein analyzing the measured response comprises estimating a difference in signal power in the measured response when the stimulation waveform is on and when it is off.

Clause 70: The method of clause 69, wherein estimating a difference in signal power comprises determining a sum of squares.

Clause 71: The method of clause 58, wherein inferring a state of the neural circuit comprises measuring an evoked compound action potential of the input neuron.

Clause 72: The method of clause 58, wherein inferring a state of the neural circuit comprises detecting presence of a signal of interest and determining a quality of the signal of interest if present.

Clause 73: The method of clause 72, wherein inferring a state of the neural circuit comprises determining a control parameter of a beneficial neuro-stimulation therapy in response to one of detecting presence and absence of the signal of interest.

Clause 74: A system comprising an implantable neuro-stimulation device configured to stimulate an input element of a neural circuit with a stimulation waveform having a predetermined characteristic, and measuring a response at an output element of the neural circuit; and a processor coupled to the implantable neuro-stimulation device to analyzing the measured response, and inferring a state of the neural circuit based on the measured response.

Clause 75: The system of clause 74, wherein the processor further infers information from the measured response for diagnostic purposes.

Clause 76: The system of clause 74, wherein the processor further infers information for a purpose of determining a parameter of a beneficial therapy.

Clause 77: The system of clause 74, wherein the processor further infers information for a purpose of determining a control parameter of a beneficial neuro-stimulation therapy.

Clause 78: The system of clause 74, wherein the processor further infers information for a purpose of determining a control parameter of a beneficial drug delivery device.

Clause 79: The system of clause 74, wherein the processor further infers information about concentration of specific neurotransmitters between neurons in the neural circuit.

Clause 80: The system of clause 74, wherein the implantable neuro-stimulation device stimulates the input element of the neural circuit with a stimulation waveform that has an auto-correlation function with a single well-defined peak.

Clause 81: The system of clause 74, wherein the implantable neuro-stimulation device stimulates the input element of the neural circuit with a pseudo-random binary noise sequence signal.

Clause 82: The system of clause 81, wherein the processor further cross-correlates the pseudorandom binary noise sequence signal at the input element with a measured response at the output element.

Clause 83: The system of clause 74, wherein the implantable neuro-stimulation device modulates the stimulation waveform between on and off states.

Clause 84: The system of clause 83, wherein the processor further estimates a difference of a specific characteristic of the measured response when the stimulation waveform is on and when it is off.

Clause 85: The system of clause 83, wherein the processor further estimates a difference in signal power in the measured response when the stimulation waveform is on and when it is off.

Clause 86: The system of clause 85, wherein the processor further estimates a difference in signal power comprises determining a sum of squares.

Clause 87: The system of clause 74, wherein the processor further measures an evoked compound action potential of the input neuron.

Clause 88: The system of clause 74, wherein the processor further detects presence of a signal of interest and determining a quality of the signal of interest if present.

Clause 89: The system of claim 88, wherein the processor further determines a control parameter of a beneficial neuro-stimulation therapy in response to one of detecting presence and absence of the signal of interest.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 36-43 are amplitude and phase spectra of estimates of ECAP and Artifact signals according to the teachings of the present disclosure.

DETAILED DESCRIPTION OF THE INVENTION

Figure 1:
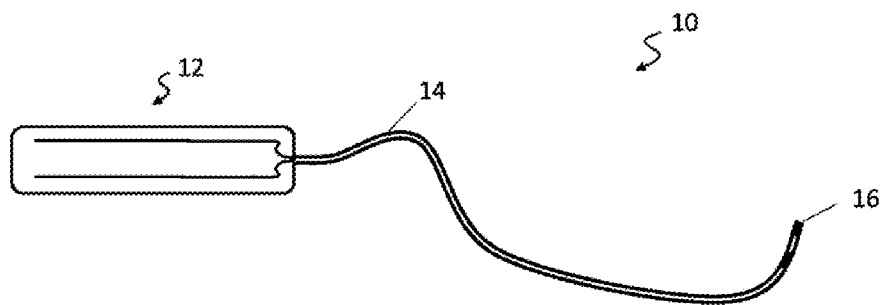
FIG. 1 is a schematic diagram of an exemplary embodiment of an implantable lead assembly 10 for a neuro-stimulation system according to the teachings of the present disclosure.

An effective implantable neuro-stimulation lead structure should possess a number of desirable characteristics, including bio-compatibility and bio-survivability. The lead should create an electric field appropriate to stimulate the target nerves, and generate minimal adverse response from the tissues to the implant. The lead structure should also have a form factor appropriate to the area of the body in which it is implanted, and should have appropriate mechanical properties to survive implantation and possible explanation.

When a lead is used that is not appropriate for a particular application, adverse events can result. For example, in occipital nerve stimulation (ONS) trials, implantable lead-related adverse events tend to stem from the fact that these procedures are currently done with commercial leads and stimulators approved for Spinal Cord Stimulation (SCS) and used "off label." In the ONS application, these leads are intended for use in central nervous system stimulation (CNSS) where they are designed to deliver stimulation targeted to very specific locations. This means the leads used in CNSS have multiple electrodes configured to allow the accurate placement of fairly localized electrical fields. Moreover, these leads are typically mechanically stiff both to ensure the lead does not move once implanted and, in some cases, to allow them to pass easily through a tuohy needle to the target tissue. These relatively stiff leads, when placed under the skin or in other locations such as for ONS, are prone to breakage, skin erosion (often resulting in infections) and lead instability due to difficulty in anchoring.

It has also been recognized that in peripheral nervous system stimulation (PNSS) applications, depending on the application, either localized or more generalized fields are used to ensure that the target nerve is properly stimulated. To achieve these larger fields using lead developed for the CNSS (designed to produce localized fields), multiple electrodes need to be activated simultaneously generally results in higher power demand and reduced battery life. Accordingly, the lead structures described herein are particularly suited to ONS therapies and PNS applications more generally. However, those skilled in the art should understand that the lead structures described herein are applicable to other forms of neuro-stimulation therapies, including for example, tibial nerve stimulation for over active bladder, glossopharyngeal stimulation for obstructive sleep apnea, trigeminal nerve stimulation for facial pain, and supraorbital nerve stimulation for headache and facial pain. The lead structure disclosed herein can also be used to stimulate or otherwise modulate nerves in or on an organ or other anatomical structure by direct stimulation of the surface of anatomical structure. For example, a conformable porous lead in accordance with the present invention may be shaped to conform to a surface contour or topology of said anatomical structure so that stimulatory current may be delivered to the surface and the associated nerves.

FIG. 1 is a schematic diagram of an exemplary embodiment of an implantable lead assembly 10 for a neuro-stimulation system according to the teachings of the present disclosure. The neuromodulation lead assembly 10 includes an electrode structure 12, a cable section 14, and a connector 16. The cable section 14 and connector 16 can be optional. The implantable lead assembly has good tensile strength, is extremely compliant, and able to resist fatigue. The lead assembly 10 also can be effectively anchored without the need for special anatomical features and can be cost effectively manufactured in a range of physical forms and electrode configurations. Moreover, the implantable lead assemblies described herein provoke a significantly reduced tissue reaction than traditional implantable leads. The minimal tissue reaction reduces the formation of fibrous tissues or capsule around the implanted lead, which may effectively increase the effective impedance of the leads.

Figure 2:
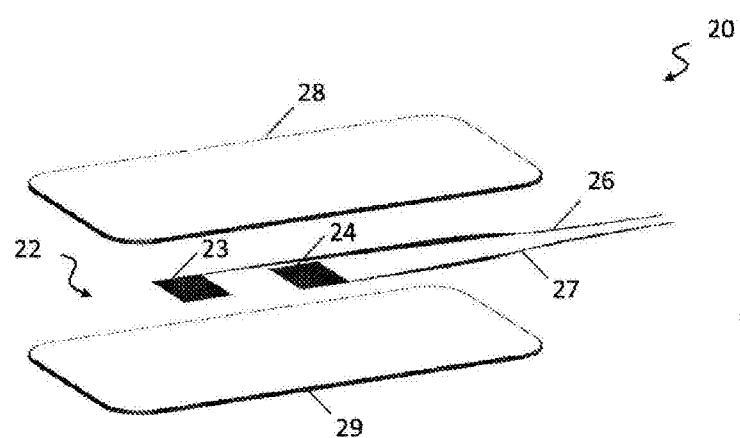
FIG. 2 is an exploded schematic diagram of a more detailed exemplary embodiment of an implantable lead assembly 20 for a neuro-stimulation system according to the teachings of the present disclosure.

FIG. 2 is an exploded schematic diagram of a more detailed exemplary embodiment of an implantable lead 20 for a neuro-stimulation system according to the teachings of the present disclosure. The exemplary implantable lead assembly 20 includes an electrode assembly 22 that includes two electrode elements 23 and 24 and two electrical connection elements 26 and 27 embedded in the porous substrate shown in parts 28 and 29. The electrode assembly may be formed from suitable bio-compatible conductive materials such as, but not limited to, Pt or PtIr, and are configured to be suitable for the specific application for which the particular lead is designed. According to one aspect of this disclosure it is possible to create electrode structures that generate optimal field structures for the target nerve. When the two substrate layers 28 and 29 form a continuous substrate, the electrode assembly 22 is held securely in place. The porous substrate formed by parts 28 and 29 has the structure of a tissue scaffold that imitates the ExtraCellular Matrix (ECM). This scaffold minimizes the fibrotic tissue reaction and allows only superficial cellular ingrowth causing the substrate to adhere to the adjacent tissues. Because the porous substrate can be engineered for good cell adhesion, a lead structure can be effectively anchored, without tissue damage, across all of the porous substrate that is exposed to the surrounding tissue. Such a lead will significantly reduce lead migrations adverse events. Such a lead may be anchored subcutaneously without a separate anchor, on internal organs, in muscles, intravenously, and around nerves. It can also be effectively anchored within the central nervous system. The ability to anchor the lead without the need for a separate anchor device also means much smaller leads can be effectively anchored. The porous substrates allows the body's electrolyte to contact the electrode integrated into the substrate and it also provides mechanical support for the electrodes and other inclusions, giving the whole lead structural integrity. The porous substrates 28 and 29 may be formed from polyurethane (PU), polytetrafluoroethylene (PTFE), Polyethylene terephthalate (PET) and other suitable bio-compatible and non-biodegradable materials now known or later developed. Substrates made from this material should have pore sizes that prevent the ingrowth of vascularized tissue. Pore sizes less than 15 µm will typically achieve this goal, and pores sizes in the range 2-10 µm are preferred. The pore size chosen for a specific lead will depend on the specific design goals for a particular lead: in general smaller pore sizes will deliver higher dielectric constants and higher lead impedances, while, in some porous substrates, such as electrospun non-woven materials, a smaller pore size provide a higher substrate strength.

Figure 3:
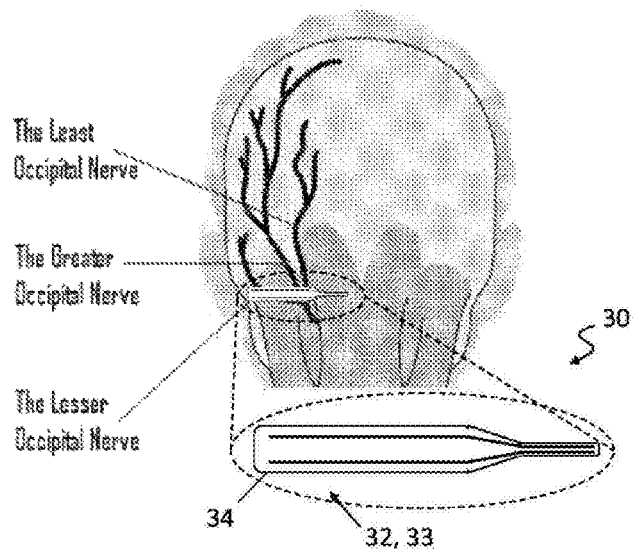
FIG. 3 is a schematic diagram of an exemplary embodiment of an implantable lead structure 30 with an electrode structure optimized for occipital nervous stimulation (ONS) for a neuro-stimulation system according to the teachings of the present disclosure.

FIG. 3 is a schematic diagram of an exemplary embodiment of an implantable lead structure 30 with an electrode structure optimized for occipital nervous stimulation (ONS) for a neuro-stimulation system according to the teachings of the present disclosure. In this example taking the form of a "patch" electrode, the elongated lead structure 30 includes two parallel electrode elements 32 and 33 embedded in a porous substrate 34. The lead structure 30 may have an exemplary length, I, in the 6-7 cm range, and an exemplary height, h, in the 6 mm range. In the exemplary placement shown in FIG. 3, the implantable lead structure 30 is able to cover the least occipital, greater occipital, and lesser occipital nerves, and generate a therapeutic electric field around these nerves.

Figure 4:
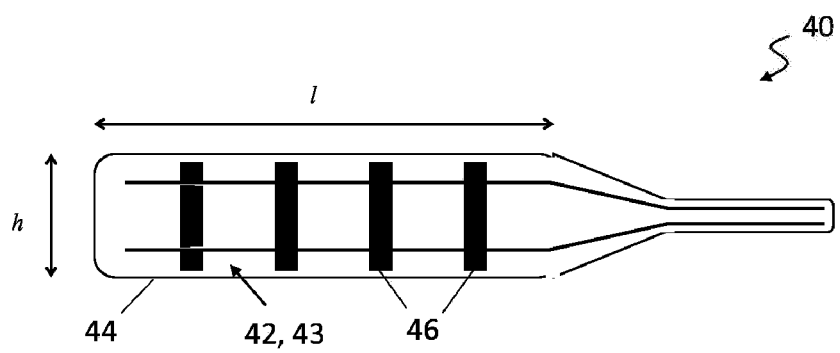
FIG. 4 is a schematic diagram of another exemplary embodiment of an implantable lead structure 40 suitable for occipital nervous stimulation (ONS) for a neuro-stimulation system according to the teachings of the present disclosure.

FIG. 4 is a schematic diagram of another exemplary embodiment of an implantable lead structure 40 suitable for occipital nervous stimulation (ONS) for a neuro-stimulation system according to the teachings of the present disclosure. The lead structure 40 is similar to that shown in FIG. 3, and includes parallel electrode elements 42 and 43 embedded in a porous substrate 44. Implantable lead structure 40 further includes masked regions 46 that can be selectively positioned in order to cover parts of the conductive electrode elements with materials to reduce or remove porosity in the substrate 44. Regions of reduced porosity may be used to insulate selected sections of the electrode element from electrolyte, reduce the effective surface area of the electrode, and/or reduce the level of adhesion within the electrode and the adjoining tissue. The "masked" region may be created by selectively making portions of the porous substrate less porous and/or adding a suitable non-porous layer within the porous substrate 44 or outside the porous substrate 44. An intermediate porous layer may be embedded within the layers forming the outer porous substrate 44, where the intermediate porous layer may have defined thereon selected regions of reduced porosity or non-porosity.

Figure 5:
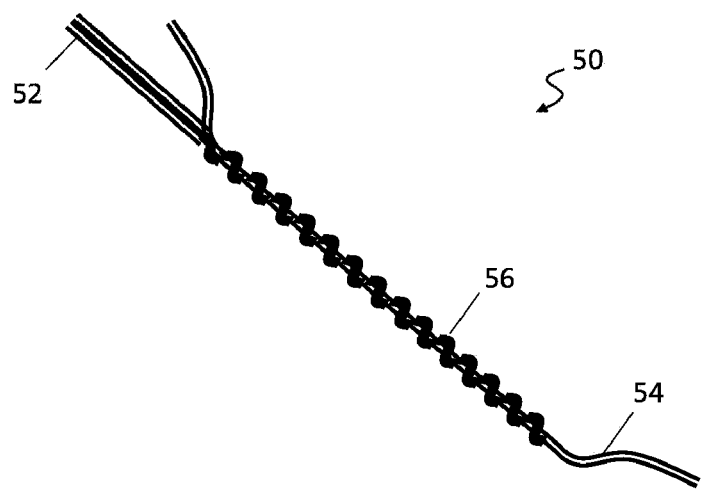
FIG. 5 is a diagrammatic illustration of an exemplary electrode construction 50 according to the teachings of the present disclosure.

According to another aspect of this invention, an implantable neuro stimulation lead may be constructed in the form of FIG. 4 with one or more substantially parallel, linear electrodes, for example in the form shown in FIG. 5, wherein the materials used are all bio-compatible and the lead structure ensures the electrodes are continuously supported by the enclosing porous substrate. Such may be made arbitrarily long and be trimmed to the appropriate length at the time of implantation. The fact that electrode structure is continuously supported by the porous substrate (i.e. there are no discrete support structures) and the use of only biocompatible materials means trimming the length of the lead will not compromise its mechanical or biocompatibility status.

Figure 4A:
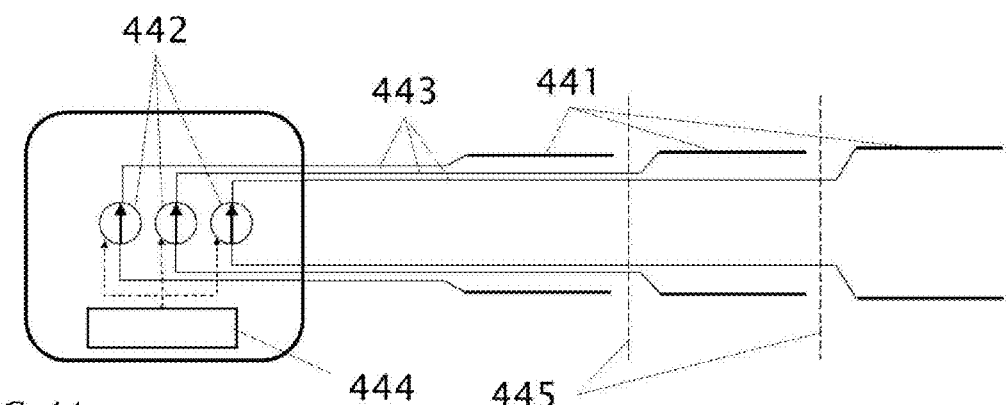
FIG. 4A is a schematic diagram of a method of making a multi-electrode device wherein the stimulation lead may be cut at well-defined locations and still be safe to use.

FIG. 4A shows a particular embodiment of a linear electrode porous lead where two or more pairs of electrodes 441 are each connected to identical current sources, 442, by connecting wires, 443. The charge on each pair or electrodes is a function of the magnitude of the current supplied by the current source and the time for which the current is allowed to flow, as controlled by the control circuit 444. If the current sources and electrodes are configured to be identical, then the one control circuit can ensure the same charge is established on each pair of electrodes. In such a configuration, the porous lead may be cut at any of the cutting lines, 445, without affecting the performance of the remaining pairs of leads. For safety the control circuit must be able to detect the absence of a pair of electrodes and disable the associated current source.

Those skilled in the art will understand that reducing length of the linear electrodes will necessarily reduce the total surface area of the electrode structure. This in turn means that the total charge that can be safely put onto the electrode will also decrease to ensure the safe charge density for the particular electrode material is not exceeded. Those skilled in the art will also understand that adjusting the length of the electrode structure will also cause the impedance of the lead to change.

According to another aspect of this invention the safe charge limit for a stimulator attached to a length adjustable lead as is described herein may be determined either manually, for example by the clinician who trims the lead measuring the revised length of the lead and calculating a safe charge limit, or automatically by the stimulator from some parameter of the lead that the stimulator can measure, for example by measuring the impedance of the adjusted lead the stimulator may infer the new length of the lead and therefore also the safe charge limit.

FIG. 5 is a diagrammatic illustration of an exemplary electrode construction 50 according to the teachings of the present disclosure. A preferred construction of the electrode element 50 is formed of a suitable mono- or multi-filament wire supported by and/or formed on a non-conductive filament. The insulated wire 52 is made from a suitable bio-compatible conductive material with some of its insulation removed to expose the inner conductive wire 54. The inner conductive wire 54 is then wound helically with a non-conductive support filament 56. This arrangement has several advantages. There is no joint required within the electrode and the electrical connection element. The wire helix formed this way is more likely to resist fatigue. The supporting filament 56 may be made from an appropriate material that the filament can induce bonding to the porous substrate, helping to anchor the lead structure in place. It should be understood that other methods for forming the electrode structures exist. For example, electrodes of more complex shape can be formed from bulk materials using a process such as Electro-Discharge Machining (EDM), milling, and stamping. Electrodes so formed can be joined to electrical connection elements by welding or other joining techniques. It will be understood by those skilled in the art that while one aspect of this invention is the use of the porous substrate to provide the greater part of the finished lead's mechanical integrity, some elements, for example the non-conductive support filament described above, may be used to provide some measure of mechanical integrity, especially during the manufacturing process.

The porous substrate is formed from a biocompatible and non-biodegradable material by one of a number of techniques, including phase separation, uniaxial freezing, micromolding, gas freezing, and non-woven textile techniques including electrospinning, and additive manufacturing techniques. The choice of material and manufacturing method depend on the particular form and mechanical properties required by the specific application. Similarly, the choice of particular substrate parameters such as pore size and void fraction is determined by the specific tissue interfaces required for the application in question.

Figure 6:
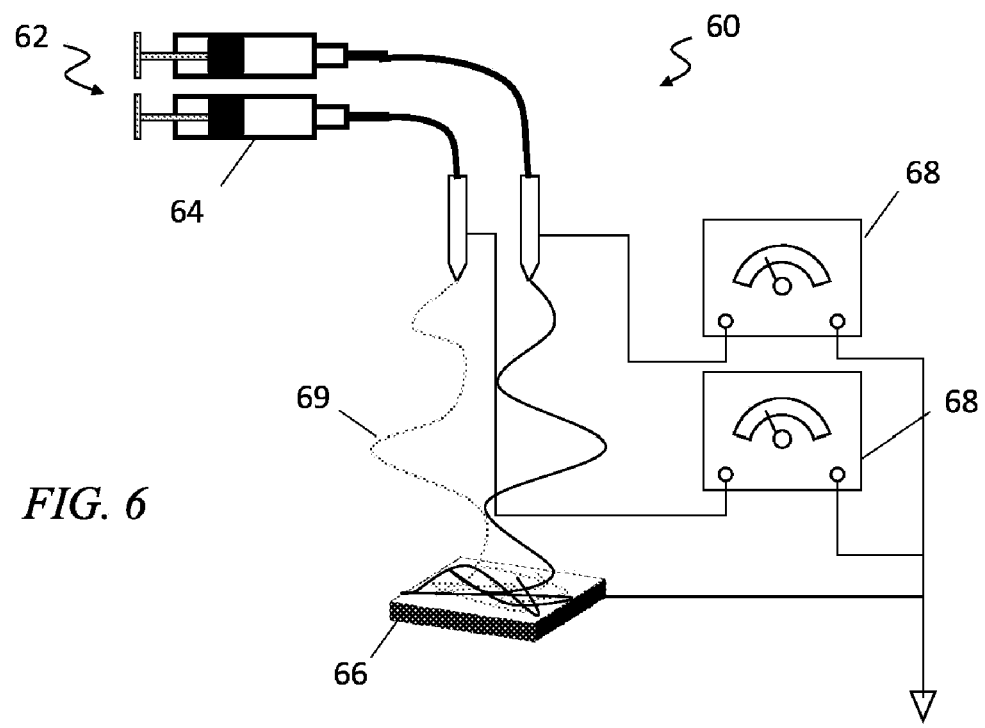
FIG. 6 is a schematic diagram of an exemplary electro spinning system 60 according to the teachings of the present disclosure.

FIG. 6 is a schematic diagram of an exemplary electrospinning system 60 for the manufacture of a non-woven porous substrate according to the teachings of the present disclosure. The electrospinning system 60 includes a liquid precursor polymer solution 62 supplied to one or more spinnerets 64 mounted above a grounded collector plate 66. A high voltage supply 68 is connected within the spinnerets 64 and the collector plate 66. The precursor polymer solution, sol-gel, particulate suspension or melt is fed to the spinnerets 64 at a controlled rate. The electric field within the tip of the spinnerets 64 and the collector plate 66 draws very fine fibers 69 that are produced from the spinnerets 64 and deposited onto the collector plate 66. As the exuded material or fiber is deposited, it fuses with other deposited fibers and forms a porous non-woven material or textile. Alternatively, the deposited fibers may be subject to appropriate post-deposition treatment to form or strengthen the bonds within the fibers, such as specific temperature and/or pressure.

In the exemplary electrospinning system 60 shown, two or more different materials may be deposited and used to form the porous non-woven material. With the right material selection, this process is able to produce porous substrates with high void fractions, small pore sizes, and good mechanical properties in sheets as thin as 100 micrometers. The porous substrate is made from the random alignment of many layers of nanofibers laid in a random pattern to produce a non-woven textile with good and isotropic mechanical properties. This embodiment can be a cost effective way to create a wide range of lead forms with good mechanical, electrical, and bio-response properties. When suitable base materials are used, such as polyurethane, the process has the property that newly spun fibers will bond to the previously spun fibers wherever the new fibers contact the fibers previously spun. The electro-spinning process uses an electrical charge to draw typically very fine fibers from a liquid form of the polymer used to form the electro-spun fiber. This liquid form may be achieved by dissolving the material in a suitable solvent or by using a molten precursor. Because the process does not require the use of coagulation chemistry or high temperatures to produce solid threads from solution, it is particularly suited to the production of fibers from large and/or complex molecules.

By adjusting the materials and key electro-spinning parameters it is possible to use this technique to make porous substrates that mimic the ExtraCellular Matrix (ECM) of different tissue types including, but not limited to, subcutaneous tissue, vascular tissue, muscle, neural tissue, and various organs. According to one aspect of this disclosure, the characteristics of the porous substrate can be adjusted to generate the desired tissue response from the tissue type where the lead is to be implanted including, but not limited to subcutaneous placement, muscular placement, internal and external vascular placements, placement in neural tissue, and placement on various organs.

Figure 7:
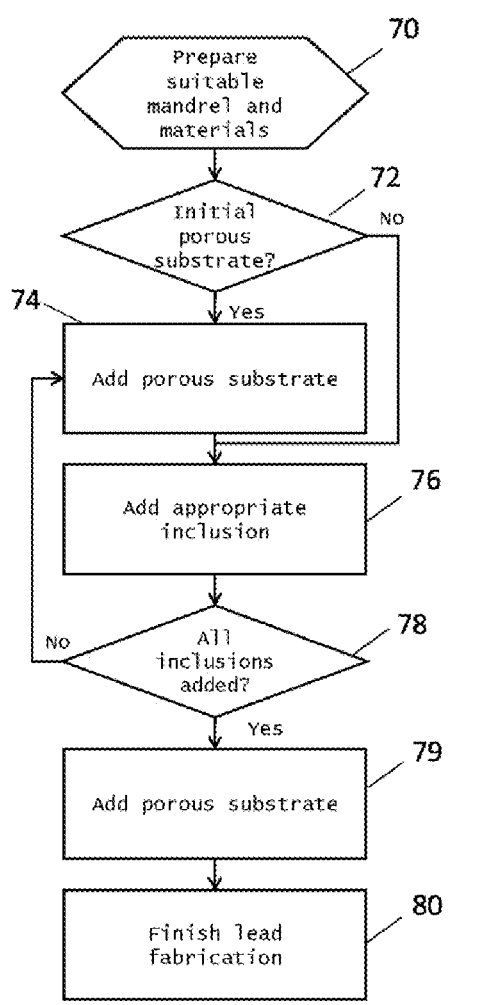
FIG. 7 is a flowchart of an exemplary process for manufacturing an implantable neuro-stimulation lead assembly or implantable neuro-stimulation system according to the teachings of the present disclosure.

FIG. 7 is a flowchart of an exemplary process for manufacturing an implantable neuro-stimulation lead assembly or implantable neuro-stimulation system according to the teachings of the present disclosure. The method described herein is applicable to the manufacture of all different forms of lead structures described in this disclosure. This approach involves forming the porous substrate in two or more stages to enclose, enmesh, embed, and support the electrode elements and any other inclusions of the neuro-stimulation system. In block 70, a mandrel of suitable dimensions and shape is prepared. In block 72, if an initial porous layer is to be formed, such first part of the porous non-woven substrate is formed over the mandrel in block 74, said mandrel being of a suitable shape for the lead to be made, for example, conformal to the shape of an organ or other tissue element whereon the lead will be placed. Thereafter, appropriate neuro-stimulation elements and inclusions are positioned on the substrate, as shown in block 76. Since such inclusions will be enclosed or enmeshed by a continuation of the electro-spinning process, the inclusions may have mechanical features designed to entangle with the electrospun fibers to assist in the integration into the porous substrate. In block 78, a determination is made as to whether all inclusions have been added, if not, another part of the porous substrate may be added in block 74, and additional inclusions incorporated in block 76. The neuro-stimulation inclusions may include electrode elements, wires, and as described in more detail below, an implantable pulse generator (IPG). When the last set of inclusions is placed then a final part of the porous substrate is laid down in block 79, and the lead fabrication is completed in block 80. Some methods of forming the porous substrates, such as electro-spinning polyurethane, naturally bond each successive part of the substrate so that the different parts are integrated into a single substrate. Other methods may require a final finishing step to bond the parts together perhaps by heat, pressure, or ultrasonic welding, or other suitable process that does not damage the substrate's structure.

Another method may be to form the porous matrix on a three dimensional mandrel, for example a cylinder, with electrodes placed in appropriate places during the formation of the porous matrix. The open form (a cylinder in the example) structure created on such a mandrel may then be collapsed in various ways by bonding different surfaces together, for example an open cylinder of porous substrate may be collapsed into a ribbon by flattening the cylinder and bonding the inner surfaces together. According to another aspect of this invention is possible to alter the material composition of the porous substrate in different locations such that two or more parts of the substrate with one material composition may be fused together or heat-set at a temperature or by a process that does not affect parts of the substrate with other material compositions. As an example it will seen that an open cylindrical structure may be created such that some part of the material composition of the inner surface of the cylindrical porous substrate melts at a lower temperature than the outer layer of the same cylindrical porous substrate. In this case, if the cylinder is collapsed to a ribbon, the facing inner surfaces of the cylindrical porous substrate will both have the low melting point material composition and may be bonded together by heat without affecting the outer surfaces of the ribbon structure. Those skilled in the art that other bonding methods such as by the application of selective solvents may be also be used to achieve this effect.

Optionally, a non-porous layer may be added to all or portions of an external surface of the porous substrate. Alternatively, the porous substrate layers may be formed and then cut into the proper shape and size before being placed over the mandrel, and laid over the neuro-stimulation elements. Further, one or more additional porous parts with masked regions may be added as intermediate layers within the two outer porous non-woven substrates.

The porous substrates may be further modified by incorporating certain inclusions, such as metal, glass, or ceramic materials of certain desirable shapes and sizes to create an enclosure, seal or barrier to moisture and oxygen if high levels of electrolyte exclusion are desired in certain regions of the implantable system. In an alternate embodiment, a laminated multilayer structure may form part of the inclusion within the porous substrates.

Another feature that may be added to the porous substrates is to form one or more anchor pads by modifying the pore size so that controlled tissue ingrowth can be achieved in selected areas of the lead structure to provide long term anchoring. In the case of an electro spun substrate, the anchor pads may be formed by changing the density of the electro-spun fibers in selected regions of the substrate. Precision deposition techniques such as near-field electro-spinning may be used to create the anchor pads. Another technique involves using a segmented collector plate to which different potentials are applied in the electro-spinning equipment. Other known techniques may be used.

Those skilled in the art will know many enhancements of this basic technique are possible. Of particular interest are the ability to form core-shell fibers (fibers with different materials in their core and outer shell), the control of the deposition pattern using high-precision deposition techniques, the control of fiber orientation, and the use of multiple die and die-free spinning methods.

Figure 8:
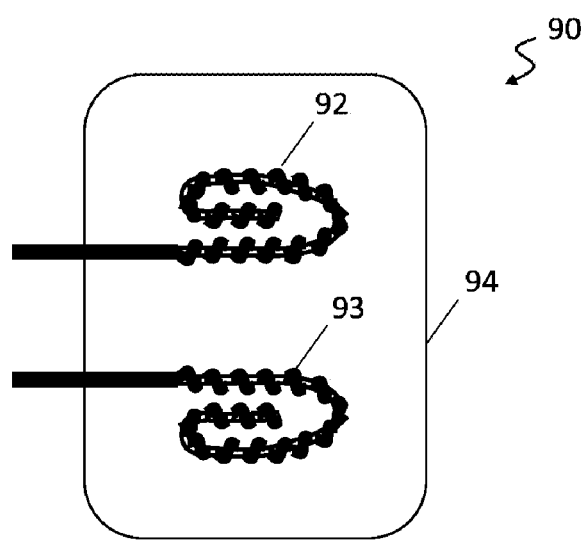
FIG. 8 is a diagrammatic illustration of an exemplary embodiment of a paddle lead structure 90 for neuro-stimulation according to the teachings of the present disclosure.

FIG. 8 is a diagrammatic illustration of an exemplary embodiment of a paddle lead structure 90 for neuro-stimulation according to the teachings of the present disclosure. This electrode configuration 90 uses the helically wrapped lead structure shown in FIG. 5 and described above. A preferred embodiment of the paddle electrode assembly 90 includes two electrode elements 92 and 93 enclosed, enmeshed, and supported by a porous substrate 94 in the manner described above.

Figure 9:
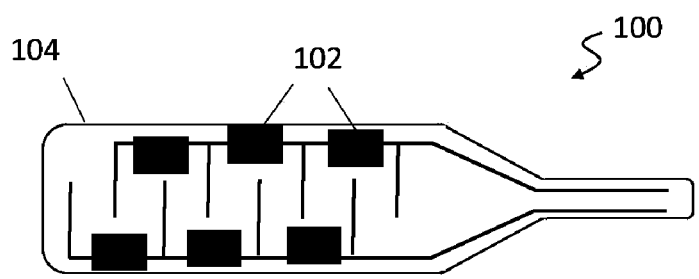
FIG. 9 is a diagrammatic illustration of another exemplary embodiment of a patch lead structure 100 according to the teachings of the present disclosure.

FIG. 9 is a diagrammatic illustration of another exemplary embodiment of a patch lead structure 100 according to the teachings of the present disclosure. Implantable lead structure 100 further includes masked regions 102 that can be selectively positioned in order to cover parts of the conductive electrode element with reduced porosity. The patch lead structure 100 may include two conductive electrode elements laid out in the lead structure in a predetermined pattern in the porous substrate 104 to create a desired electrical field, with selective regions passed through by the electrode element masked to create regions of reduced porosity in the combined substrate layers. Regions of reduced or no porosity may be used to insulate selected sections of the electrode element from electrolyte, reduce the effective surface area of the electrode, and/or reduce the level of adhesion within the electrode and the adjoining tissue. The "masked" region may be created by selectively making portions of the porous substrate less porous and/or adding a suitable non-porous layer in within the porous substrate or on the surface of the porous substrate. An intermediate porous layer may be embedded in the porous substrate, where the intermediate porous layer may have defined thereon selected regions of reduced porosity or non-porosity.

Figure 10:
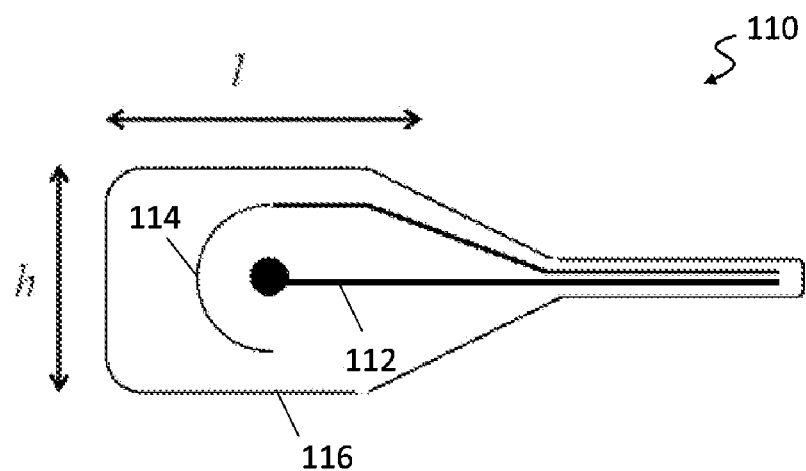
FIG. 10 is a diagrammatic illustration of an exemplary embodiment of another patch lead structure 110 for neuro-stimulation according to the teachings of the present disclosure.

FIG. 10 is a diagrammatic illustration of an exemplary embodiment of another patch lead structure 110 for neuro-stimulation according to the teachings of the present disclosure. The patch lead structure 110 includes two electrode elements 112 and 114 laid out in a predetermined pattern within a porous substrate 116 to create a desired electrical field. The patch lead structure 110 includes a first conductive electrode element 112 laid out in a linear fashion with a terminal point, and a second conductive electrode element 114 laid out in a circular arc around the terminal point. As described above, the electrode elements 112 and 114 are enclosed and enmeshed within two or more parts of the substrate 116 of suitable shape and dimensions.

Figure 11:
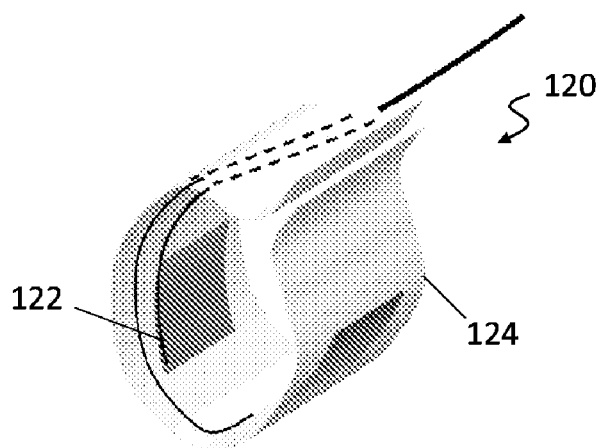
FIG. 11 is a diagrammatic illustration of an exemplary embodiment of a cuff lead structure 120 for neuro-stimulation according to the teachings of the present disclosure.

FIG. 11 is a diagrammatic illustration of an exemplary embodiment of a cuff lead structure 120 for neuro-stimulation according to the teachings of the present disclosure. The cuff lead structure 120 is generally cylindrical in shape and substantially surrounds the circumference of a nerve and suture closed. The cuff lead structure 120 may be formed by embedding the conductive electrode elements 122 within the porous substrate 124 of a desirable shape and size and formed over a cylindrical mandrel as described above.

Figure 12:
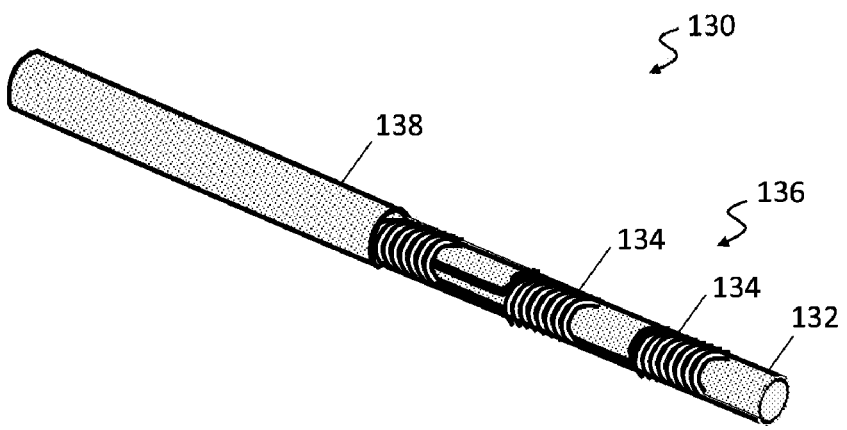
FIG. 12 is a diagrammatic illustration of an exemplary embodiment of a catheter style lead structure 130 for neuro-stimulation according to the teachings of the present disclosure.

FIG. 12 is a diagrammatic illustration of an exemplary embodiment of a catheter style lead structure 130 for neuro-stimulation according to the teachings of the present disclosure. The catheter style lead structure 130 may be manufactured by using a cylindrical mandrel which is rotated about its axis during the electrospinning process to create a porous substrate in a cylindrical form. The first part of the porous substrate 132 is formed on the cylindrical mandrel, then an insulated biocompatible wire is prepared by stripping the insulation from one end of the wire 134. The uninsulated length of wire 134 is then wound around the first part of the porous substrate 132 forming an electrode element 136, and the insulated part of the wire is laid on the first part of the porous substrate parallel to the axis of the cylindrical substrate to form the electrical connecting element 134. This process may be repeated one or more times to create the desired number of electrode elements. This process may also be repeated at the distal end of the cylindrical mandrel to form a second set of lead structures that may be later uncovered to form connector contacts. Once all of the electrode inclusions are in place, a second part of the porous substrate 138 is then laid down on the cylindrical mandrel to cover the electrode elements. One or more regions of the lead structure may be masked to create reduced or no porosity. Once removed from the cylindrical mandrel, the finished lead will have a central lumen in which a stylet may be placed to temporarily stiffen the lead structure during implantation.

Figure 13:
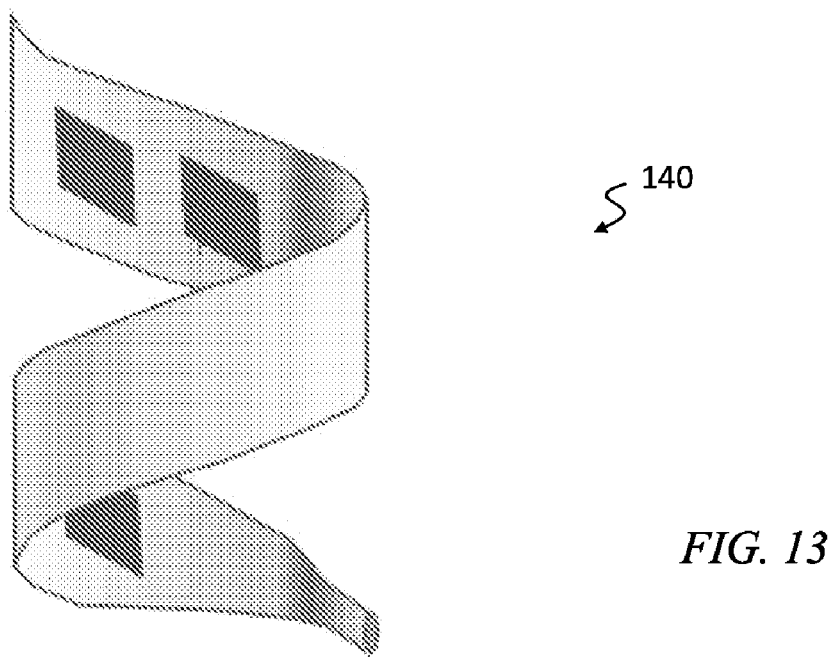
FIG. 13 is a diagrammatic illustration of an exemplary embodiment of a helical lead structure 140 for neuro-stimulation according to the teachings of the present disclosure.

FIG. 13 is a diagrammatic illustration of an exemplary embodiment of a helical lead structure 140 for neuro-stimulation according to the teachings of the present disclosure. The helical lead structure 140 includes electrode elements embedded within a helical shaped porous substrate, which may also be formed over a suitably shaped mandrel. The helical lead structure 140 may be formed by forming a first part of the porous substrate around a cylindrical mandrel of a suitable diameter, rotating the mandrel as the substrate is formed. The electrode elements and insulated connector wires are then laid over the first part of the porous substrate in a predetermined pattern, and formation of the porous substrate is then continued over the electrode elements.

Figure 14:
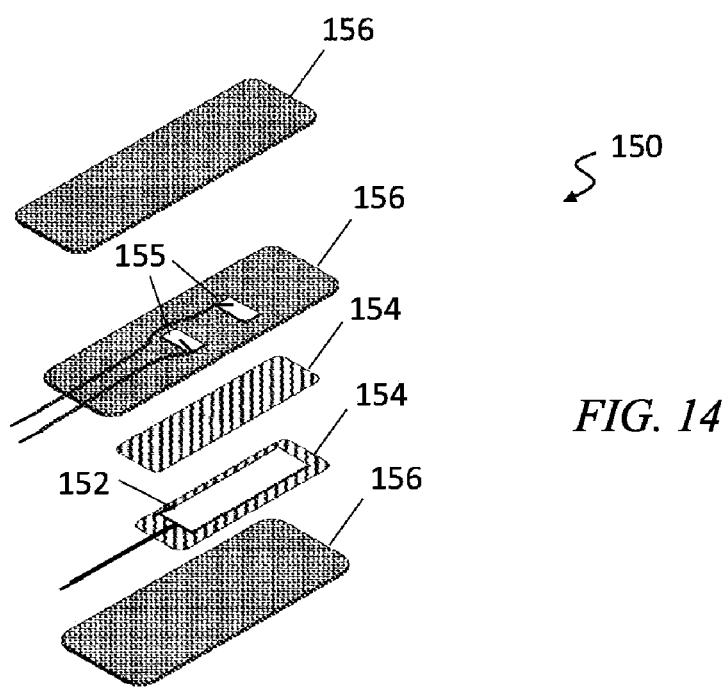
FIG. 14 is an exploded view of an exemplary embodiment of an implantable lead assembly 150 with a field shaping element according to the teachings of the present disclosure.

According to a further aspect of this disclosure, the lead assembly 150 shown in FIG. 14 may include a field shaping element called a "buried electrode" 152 that is connected to the stimulator but electrically isolated from the tissue by insulating layers 154. Such an electrode 152 is capacitively coupled to the tissue and would hold any charge placed on the electrode for a relatively long time. Accordingly, the buried electrode 152 can be placed in an appropriate location and pre-charged to an appropriate charge density, prior to the stimulation cycle, to influence the shape of the field created during the stimulation cycle. The one or more field shaping elements or buried electrodes may be made from suitable bio-compatible conductive materials such as, but not limited to, Pt or PtIr which may be coated with suitable bio-compatible non-conductive or insulative materials, and which may be connected to sources of specific electrical potentials for the purpose of shaping the electrical field created by the one or more electrode elements. These field shaping elements may also embody features intended to relieve strain and improve their resistance to fatigue. As in other lead assemblies, lead assembly 150 further includes electrode elements 155 and leads that are enclosed and encased in porous substrates 156.

Figure 15:
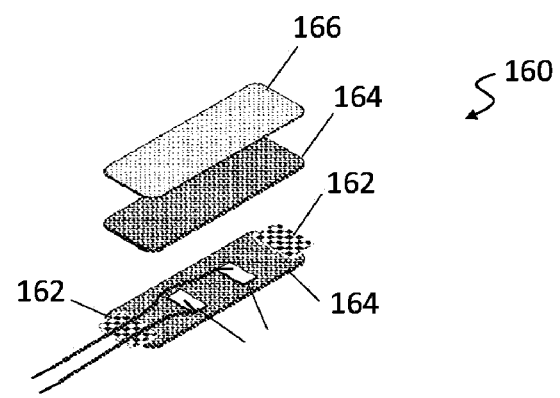
FIG. 15 is an exploded view of an exemplary embodiment of an implantable lead assembly 160 with an intermediate layer or feature according to the teachings of the present disclosure.

According to another aspect of this disclosure shown in FIG. 15, a lead assembly 160 may include an intermediate layer or feature 162 of suitable porosity that is embedded in the porous substrate 164, such that some parts of the intermediate porous layer of feature 162 extend beyond the porous substrate 164 and any impervious impregnation material layer 166 described above. The porosity of the part of this intermediate layer 162 which extends beyond the impervious impregnation material 166 is chosen to allow the ingrowth of tissue into that part of the layer to aid in anchoring the lead in the tissue. It should be understood that this "anchoring" structure need not be continuous, but tailored to ensure just as much anchoring force as is required.

Figure 16:
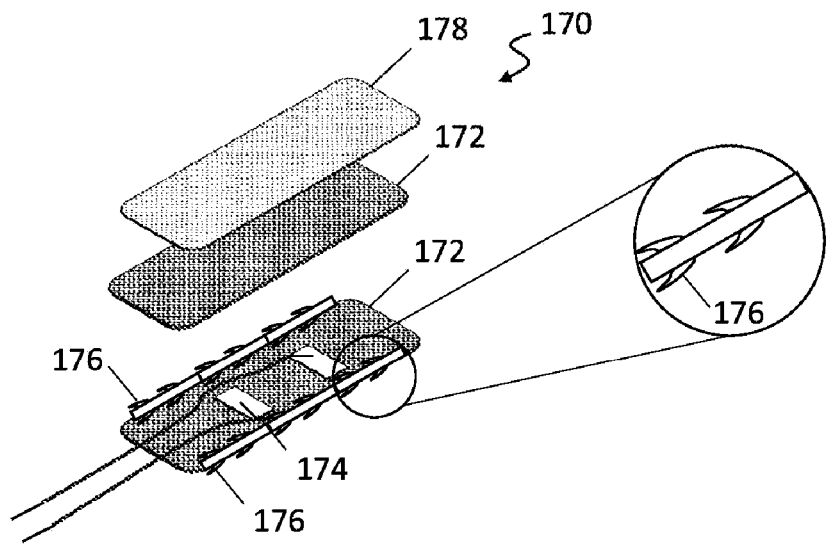
FIG. 16 is an exploded view of an exemplary embodiment of an implantable lead assembly 170 with temporary or permanent mechanical properties according to the teachings of the present disclosure.

According to a further aspect of this disclosure shown in FIG. 16, a lead assembly 170 may have temporary and permanent mechanical properties added to those of the underlying porous substrate 172 by the inclusion of resorbable or non-resorbable elements that are made from a biocompatible and resorbable or non-resorbable material in addition to the electrode elements 174. These inclusions may be included for several reasons including but not limited to ensuring that the device permanently holds a particular shape, to impart specific non-isotropic stiffness properties, to providing temporary stiffness to the lead to improved handling during implantation, and/or providing for short term anchoring after placement. The added features may include barbed features 176 on the edges of the porous substrate, for example. The example shown further includes an impervious layer 178 above the porous substrate layer 172.

The basic cable section of the lead assemblies may be manufactured as described above and then coated in a bio-compatible and readily soluble material such as PolyEthelyne Glycol (PEG) Wax or Polyvinyl Acetate (PVA). Once coated, a second enclosing layer, possible with an anchor structure as described above, may be formed around the lead using any of the construction methods described herein. Once the enclosing layer has been formed, the soluble material is removed creating a cable section which is entirely enclosed in but not coupled to the outer enclosing layer. The advantage of this construction is that if there is a need to replace the lead post-implantation, the lead can be unplugged from the implantable pulse generator and the cable section withdrawn by pulling it through the enclosing layer which will remain in place, forming a guide-way for the cable section of the replacement lead to be passed through.

The connector section can be made by the following steps: suitable mating structures for the connectors being used, made from a biocompatible metal (for example PtIr alloy), are mounted on an appropriate supporting element such as a polyurethane rod; joining the conductors in the cable section to the suitable mating structures using an appropriate bonding method (e.g., laser welding, pressure welding, spot welding etc.); encasing the connector section in a suitable flexible biocompatible material such as polyurethane or silicone; and a finishing process is used to ensure the metal structures are free from any insulating materials (such as flash from the previous step) and overall structure is appropriately smooth.

In a preferred embodiment, the connector is a canted coil connector (such as a BalSeal™ connector) so that the suitable mating structure is a cylinder with a diameter of around 1.2 mm and a length around 2-3 mm. The polyurethane supporting rod should be sufficiently long and stiff to allow the implanting surgeon to be able to easily push the connector structure into the connector. The preferred encapsulating material is silicone for compatibility with the cable section and the finishing process is cylindrical grinding.

Figure 17:
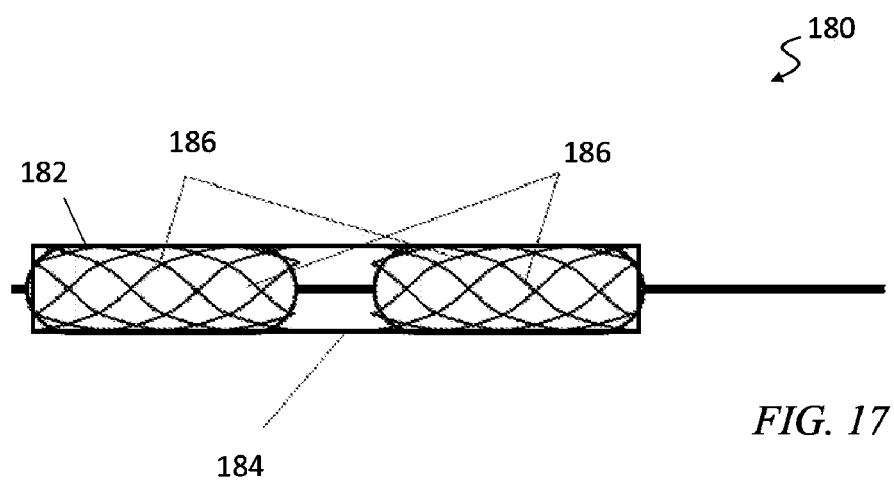
FIG. 17 is a diagrammatic illustration of an exemplary embodiment of an implantable transvenous lead structure 180 for neuro-stimulation according to the teachings of the present disclosure.

FIG. 17 is a diagrammatic illustration of an exemplary embodiment of an implantable transvenous lead structure 180 for neuro-stimulation according to the teachings of the present disclosure. The transvenous lead structure 180 is constructed by embedding electrically conductive elements of the appropriate structure and other inclusions in a porous bio-compatible substrate such as described above. In an exemplary embodiment, two wire stent electrodes 182 are embedded in a suitable porous substrate 184 and the entire assembly is mounted over one or more balloons 186 that are attached to a suitable catheter (similar to a balloon catheter used in angioplasty procedures). The transvenous lead structure 180 may be introduced into a vein or other blood vessel, advanced to a desired stimulation site, and then anchored in place by expanding the balloon to secure the stents against the wall of the vein or other blood vessel. Since nerve and blood vessels often join visceral organs in much the same place, this approach provides an alternative to reaching stimulation sites that are difficult to access otherwise. In an alternate embodiment, the two wire stent electrodes 182 are replaced with a simple wire electrode mounted on a resorbable stent structure and embedded in a suitable porous substrate. This structure is implanted in the same manner as described above with the resorbable stent structures designed to secure the lead in place until the porous substrate has adhered to the wall of the blood vessel, after which time the stent structure is resorbed leaving less structure within the blood vessel. In both embodiments it will be plain to those skilled in the art that more than two electrode structures can be integrated into a single lead.

Figure 18:
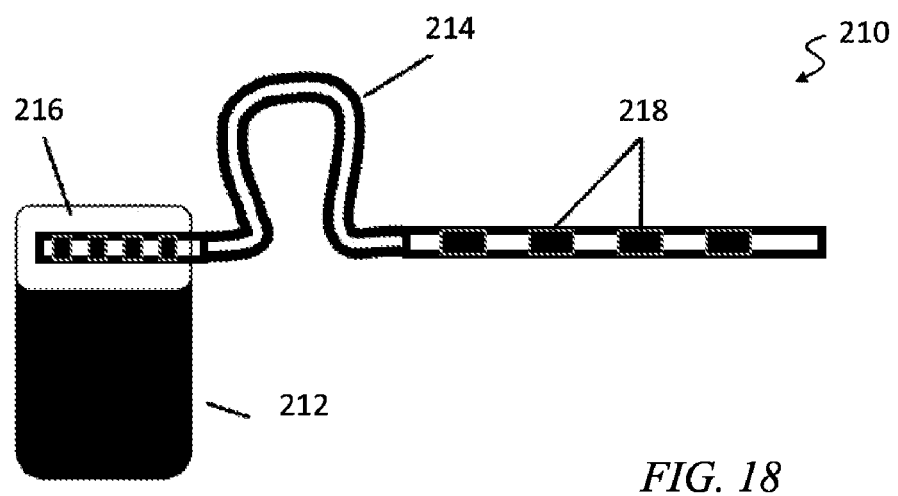
FIG. 18 is a schematic diagram of an exemplary embodiment of an implantable neuro-stimulation system 210 according to the teachings of the present disclosure.

FIG. 18 is a schematic diagram of an exemplary embodiment of an implantable neuro-stimulation system 210, which may include an energy storage device such as a battery, sometimes referred to as an active implantable medical device (AIMD), or a passive device without an included energy source and be powered by transcutaneous electromagnetic power transfer, sometime called an "RF device," according to the teachings of the present disclosure. The implantable neuro-stimulation system 210 is suitable for implantation in a wide variety of locations in the human body and particularly suitable for peripheral neuro-stimulation. The implantable neuro-stimulation system 210 includes an implantable pulse generator (IPG) 212 which is coupled to a lead assembly 214 by a connector assembly 216. The lead assembly 214 further connects the implantable pulse generator 212 to one or more electrode elements 218. The implantable neuro-stimulation system 210, including the implantable pulse generator 212, connector assembly 216, lead assembly 214, and electrode elements 218, are designed and manufactured to be implanted in a patient's body for neuro-stimulation therapies. The implantable pulse generator 212 is designed to be implanted in the patient's body at a suitable implantation site, and the electrode elements 218 are generally implanted and located away from the implantation site and close to a preferred stimulation site rather than remotely at another location in the patient's body.

Figure 19:
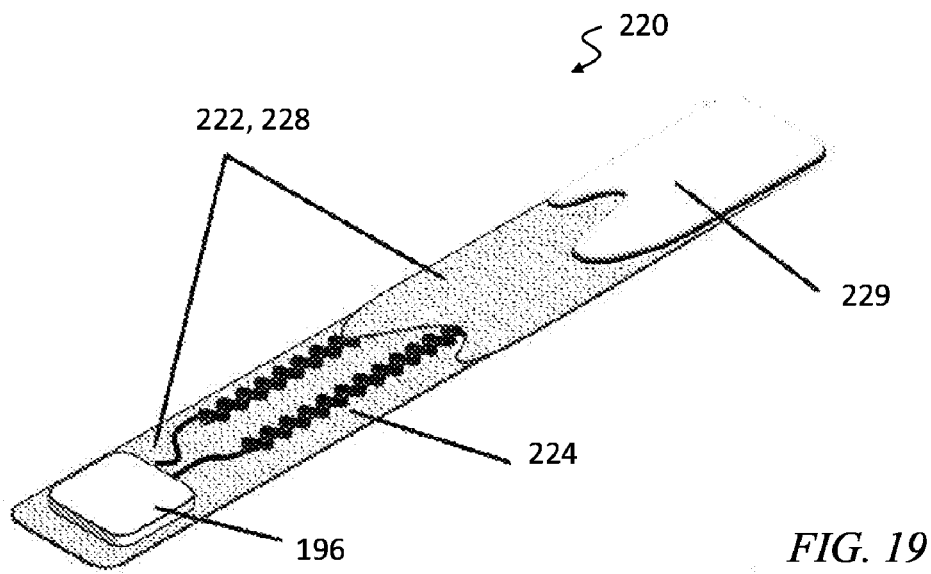
FIG. 19 is a diagrammatic diagram of an exemplary embodiment of an implantable neuro-stimulation system 220 according to the teachings of the present disclosure.

FIG. 19 is a diagrammatic diagram of an exemplary embodiment of an implantable neuro-stimulation system 220 according to the teachings of the present disclosure. An initial part of the porous substrate 222 is formed or laid down. Two electrode assemblies 224 and an impervious package 226 are then placed on the initial part of the porous substrate 222. The two electrodes 224 each comprises an electrode element and an electrical connection element, and the electrical connection element is further connected to electrical feedthroughs in the impervious package 226. A second part of the porous substrate 228 is formed or laid down over the electrode inclusions. In the figure this second part 228 is shown cut-away for clarity. When the parts 222 and 228 are completed, the inclusions 224 and 226 are held in place by the now single substrate that encloses and supports the electrode assemblies. In the example described herein a layer of non-porous material 229 may be further added to one side of the porous substrate 228. The implantable neuro-stimulation system 220 therefore encompasses the lead assembly integrated with the implantable pulse generator to form a single device that may be implanted at the stimulation site. One or more additional lead assemblies may be connected to the same pulse generator at the first stimulation site but implanted in other stimulation site(s) if desired.

It will be evident to those skilled in the art that such an implantable device 220 will be thin and extremely compliant, it will create a broad electric field running parallel to the narrow dimension of the substrate, and it will have good tissue adhesion on the bottom face. If the porous substrate is made from a non-woven textile, this device will also have good tensile strength. In the preferred embodiment, the porous substrate is formed from a non-woven fabric or material produced using, for example, the electro-spinning process that uses an electrical charge to draw typically very fine fibers from a liquid form of the polymer used to form the electro-spun fibers. This liquid form may be achieved by dissolving the material in a suitable solvent or by using a molten precursor. Because the process does not require the use of coagulation chemistry or high temperatures to produce solid threads from solution it is particularly suited to the production of fibers from large and/or complex molecules. Those skilled in the art will appreciate that other electric fields, appropriate to the application, can be created by different electrode arrangements within the porous substrate.

Figure 20:
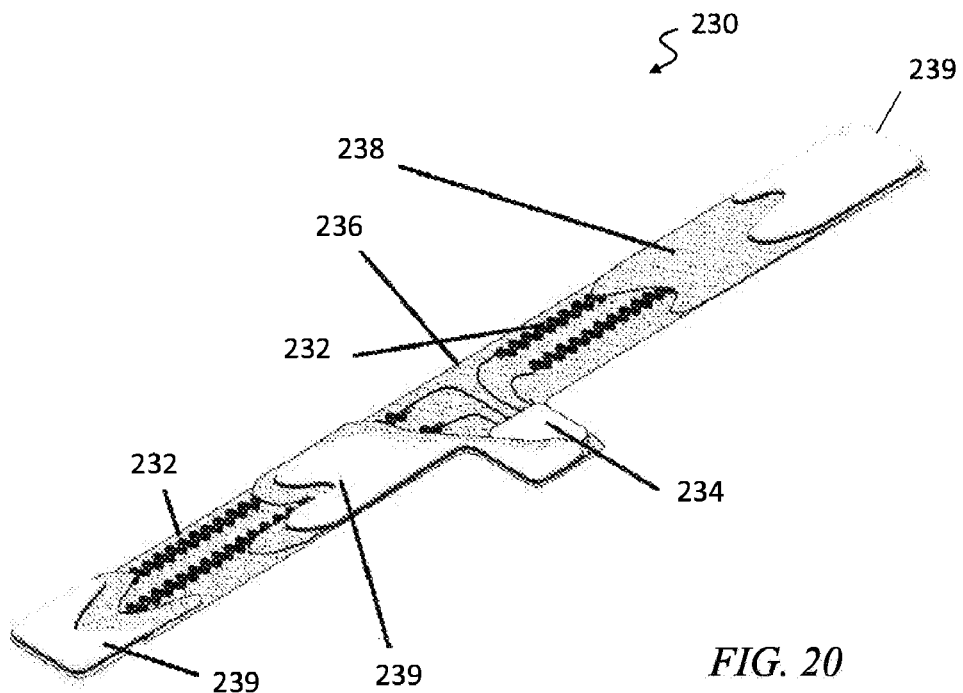
FIG. 20 is a diagrammatic illustration of an exemplary embodiment of an implantable neuro-stimulation system 230 for ONS application according to the teachings of the present disclosure.

FIG. 20 is a diagrammatic illustration of an exemplary embodiment of an implantable neuro-stimulation system 230 for ONS application according to the teachings of the present disclosure. The implantable neuro-stimulation system 230 includes four electrode structures 232 and an impervious package 234 (enclosing the circuitry of an implantable pulse generator) enmeshed, enclosed, and supported by a suitable porous substrate 236 and 238. In this embodiment, the impervious package 234 is used to contain and protect the electronic circuitry operable and configured to generate the electrical pulse waveforms used for neuro-stimulation therapies. In this embodiment, one side of the substrate is further covered or infiltrated with a non-porous material 239 shown in cut-away. The four electrodes 232 are disposed as two pairs of electrodes where the electrodes in each pair are substantially parallel and typically separated by a desirable distance, e.g., 3 mm. For ONS, the two pairs of electrodes are typically 6-7 cm long and are placed above and to the left and right of a centrally located impervious package 234 as shown in FIG. 20. Such an electrode configuration is configured to generate a broad stimulation field within the two parallel electrodes on each side of the device.

It is well known that polymers have inherently high permeability to moisture and if high levels of electrolyte exclusion are required in a particular design, for example to protect electronic components incorporated in the device, then specific hermetic, impervious, or moisture resistant structures may be included in the porous matrix. These inclusions may include metal, glass or ceramic enclosures, or enclosures formed using a laminate design. Such laminated designs are multilayered structures with materials specifically chosen to achieve a seal or barrier. Such layers may include metal foils as moisture and oxygen barriers.

To achieve a suitably small volume, the implantable neuro-stimulation system 230 may be powered by the transfer of electromagnetic energy through the skin from an external transmitting device. In this case the impervious package may also contain a coupling device, an antenna, coil or other device, to receive the transmitted electro-magnetic energy. It should be noted that the implantable neuro-stimulation system 230 may incorporate lead assemblies and other inclusions described above and may take the form of any variety of shapes.

Figure 21:
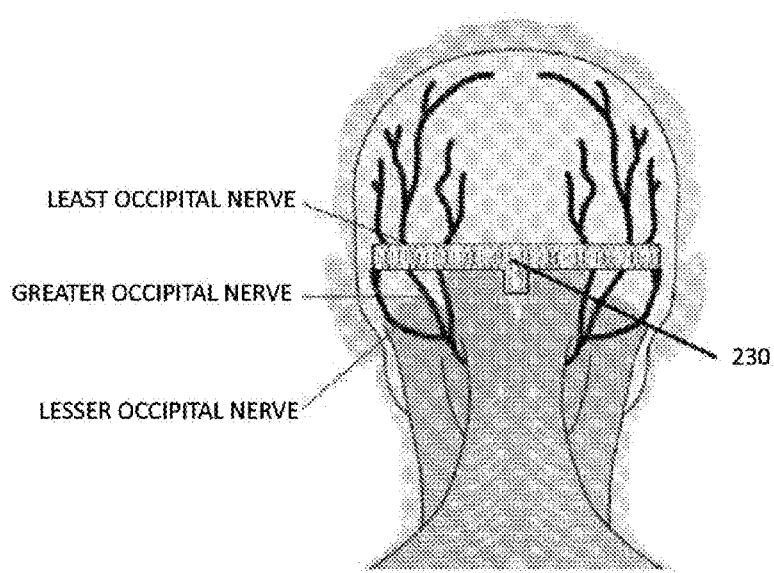
FIG. 21 is a diagrammatic illustration of a preferred placement location of an implantable neuro-stimulation system 203 for ONS application according to the teachings of the present disclosure.
Figure 22:
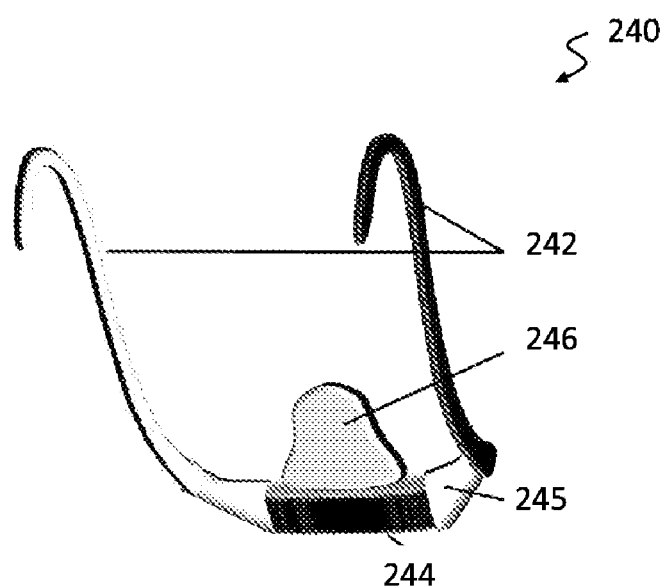
FIGS. 22 and 23A-D are diagrammatic illustrations of an exemplary embodiment of a neuro-stimulation system 240 incorporating a wearable external transmitting device according to the teachings of the present disclosure.
Figure 23A:
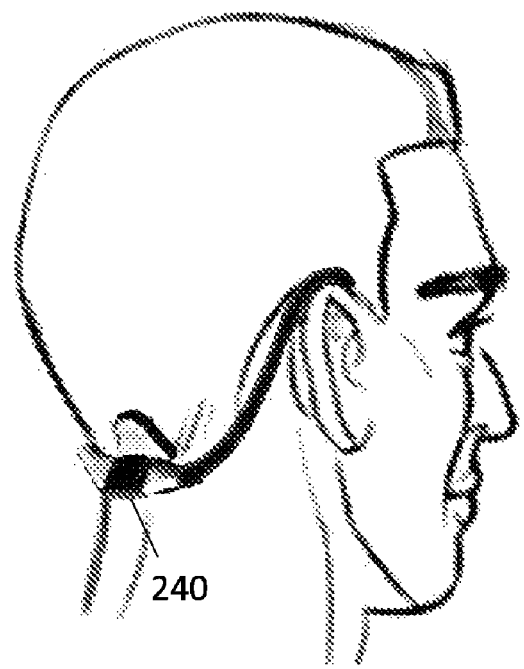
Figure 23B:
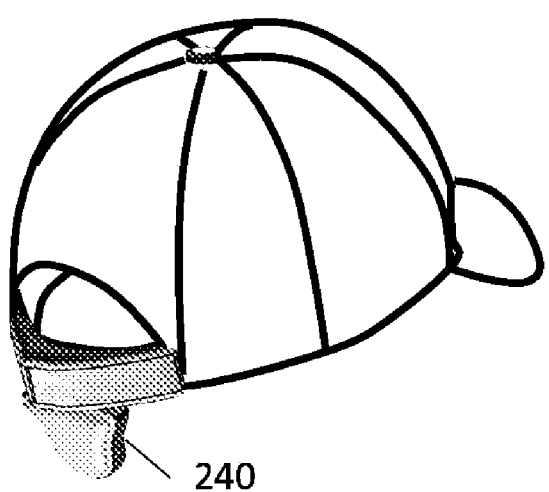
Figure 23C:
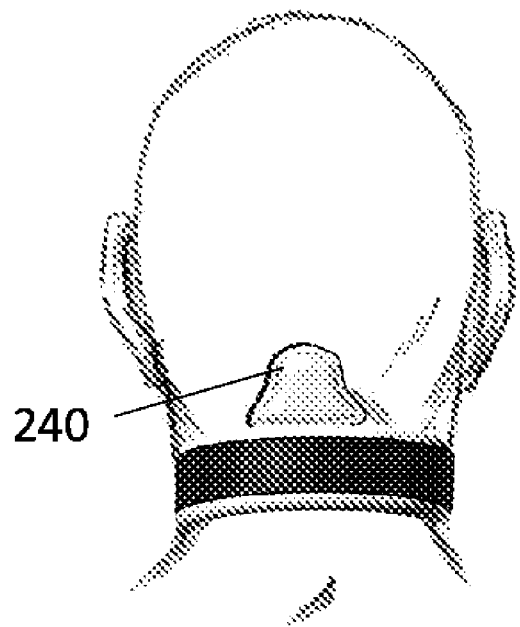
Figure 23D:
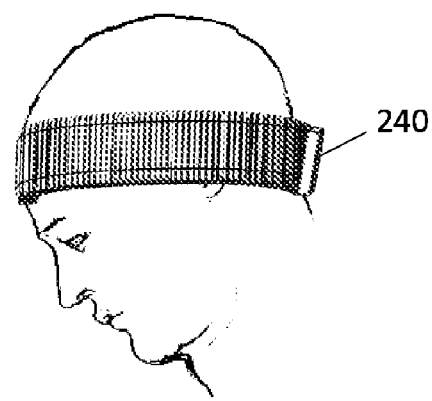

FIG. 21 is a diagrammatic illustration of a preferred placement location of an implantable neuro-stimulation system 230 for ONS application according to the teachings of the present disclosure. The implantable neuro-stimulation system 230 is implanted so that the electrode elements cover the three branches of the occipital neve. The device 230 is placed below the skin and above the branches of the occipital nerve with the side with the non-porous coating facing away from the occipital nerve. In this location the device will generate a field parallel to those nerves. Since the resulting device 230 is very thin (less than 0.5 mm thick in the lead structure) and very compliant, it also addresses the skin erosion and lead fracture adverse events. Finally, since the porous substrate can be engineered for good cell adhesion, a lead based on this invention will be effectively anchored across its entire face and will significantly reduce lead migrations adverse events Optional areas of non-porous coating or infiltration on one or more surfaces of the device 230 may be used to insulate one side of the electrode structure from electrolyte and thereby direct the stimulation field away from that side, or it may be done to modify the surface properties of the structure to achieve a different degree of cell adhesion. This can be achieved, for example, by spraying, applying or infiltrating liquid silicone to the appropriate surfaces of the structure. It may also be achieved by over-molding suitable materials, such as polyurethane, over the appropriate surfaces of the structure. Such coating or infiltration processes may also be used to ensure the electrode structure assumes a particular form.

FIGS. 22 and 23A-D are diagrammatic illustrations of an exemplary embodiment of a neuro-stimulation system 240 incorporating a wearable external transmitting device according to the teachings of the present disclosure. To reduce the volume of the implanted component it is possible to remove the battery from the implanted hermetic container and instead power the implanted components by wireless induction through the skin. An electrical coil or other means of receiving energy and/or information are enclosed inside the implanted package, which receives power and/or data by inductive or radio-frequency (RF) coupling to a transmitting coil placed outside the body. According to another aspect of the disclosure, the electromagnetic energy required to power the implanted neuro-stimulation device can be provided by a transmitting device 240 in the general form shown in FIGS. 22 and 23A-D. The external transmitting device 240 shown in FIG. 23A includes ear hooks 242 to secure the device 240 to the wearer's ears, an enclosure to contain electronic circuitry and power storage elements 244 as are required for the proper operation of the transmitting device 240. The device 240 further includes adjustment devices 245 on either sides of the electronic circuitry package 244 allows the adjustment and repositioning of the coupling assembly 246 so that it sits comfortably at the base of the wearer's skull. The external transmitting device 240 is coupled to a coupling assembly 246 that includes an antenna, coil, or other devices to transmit power to and receive data from the implanted neuro-stimulation system. It will be understood by those skilled in the art that other forms of external transmitting device are possible, including transmitting devices integrated into headphones, hat, headband, necklace, eyeglasses, purse, collar, Velcro patch, or other apparatus (examples shown in FIGS. 23B-D) capable of supporting the transmitting coil proximal to the implanted receiving coil.

Neuro-stimulation therapies involve delivering a particular pattern of stimulation pulses to a neural tissue in question. Such patterns are defined by the width, the repetition rate (or frequency) and amplitude of the stimulation pulses. Neuro-stimulators are commonly able to store one or more such patterns as a "program" and a patient may be able to select within different programs for different circumstances. Sometimes these patterns are made more complex by having the neuro-stimulator cycle within two or more pre-defined patterns to address two therapeutic goals at once. This is commonly known as "cycling." Sometimes the neuro-stimulator may cycle within a predefined pattern and no stimulation. This is commonly known as "burst mode." According to one aspect of this disclosure, a neuro-stimulator may concurrently run two or more stimulation patterns to achieve more complex therapeutic outcomes.

Figure 24:
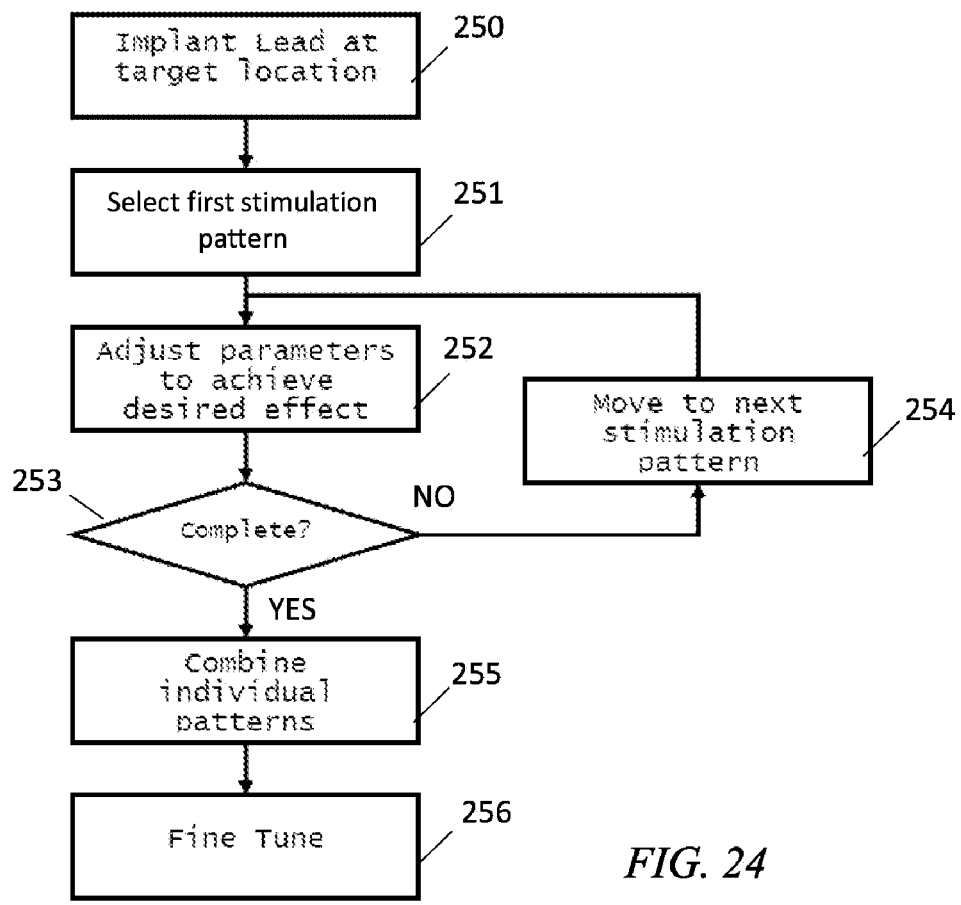
FIG. 24 is a flowchart of an exemplary process for establishing and combining multiple stimulation patterns into a composite stimulation pattern for a neuro-stimulation system according to the teachings of the present disclosure.

FIG. 24 is a flowchart of an exemplary process for establishing and combining multiple stimulation patterns into a composite stimulation pattern for a neuro-stimulation system according to the teachings of the present disclosure. In block 250, the neuro-stimulation lead structure or implantable neuro-stimulation system is implanted at the target simulation location in the patient's body. In block 251, a first stimulation pattern is selected. Thereafter, the various parameters of the first stimulation pattern, such as frequency and amplitude are adjusted to achieve the desired effect, as shown in block 252. A determination is made in block 253 as to whether the process is completed. If the process is not complete, the next stimulation waveform is added, as shown in block 254. In block 252 the parameters of the next pattern are adjusted to achieve the desired effect. In block 253, another verification is made whether all of the desired stimulation patterns have been added. If not, then further waveforms are added, but if all of the waveforms have been added, then the patterns are combined in block 255. In block 256, the combined stimulation patterns can be fine-tuned to the desired outcome.

Figure 25:
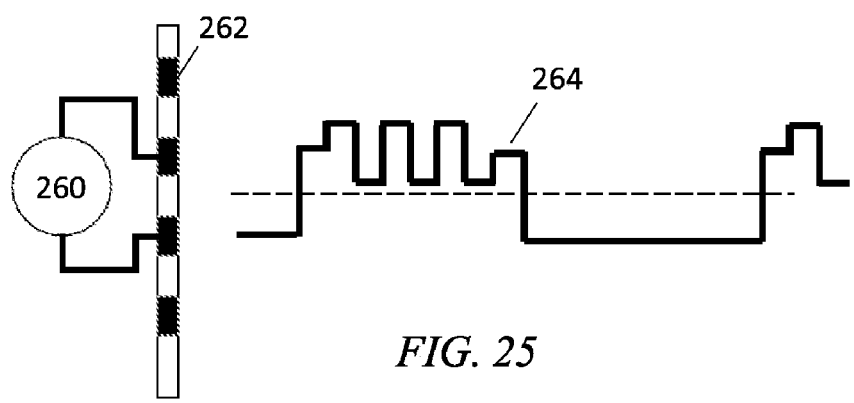
FIG. 25 is a diagrammatic illustration of an exemplary composite waveform that includes a CBAC (charge-balanced alternating current) waveform superimposed onto one phase of a CBDC (charge-balanced direct current) waveform for neuro-stimulation according to the teachings of the present disclosure.

FIG. 25 is a diagrammatic illustration of an exemplary composite waveform that includes a CBAC (charge-balanced alternating current) waveform superimposed onto one phase of a CBDC (charge-balanced direct current) waveform for neuro-stimulation according to the teachings of the present disclosure. Because stimulation paradigms that have a prolonged net DC component may lead to the production of toxic electro-chemical products, it is necessary to ensure no net DC is present in a stimulation paradigm. This can be achieved by active charge balancing (where each anodic stimulation pulse is balanced by cathodic stimulation pulse of equal charge) or by passive charge balancing where a capacitor of appropriate size is installed in the electrode circuit. Charge is stored in the capacitor during the stimulation pulse then "recovered" after the pulse as the capacitor discharges. Typically, the time constants for the capacitive recovery circuit are such that it can only be used for relatively low frequency stimulation paradigms. Since a stimulation paradigm should not present a net DC component in the long term, it will be understood by those skilled in the art that the term "DC stimulation" refers to a charge-balanced direct current (CBDC) stimulation paradigm where relatively long stimulation pulses, in the order of 10 seconds, are balanced with pulses of equal and opposite charge. CBDC waveforms may be more accurately described as low or very low frequency charge balanced alternating current (CBAC) waveforms. For clarity the terms CBDC (Charge Balanced Direct Current) is used for the nerve block stimulation and CBAC (Charge Balanced Alternating Current) is used for the nerve recruitment stimulation waveform.

According to one aspect of this invention, a stimulation paradigm that combines a CBDC nerve block pulse with a burst, cycle or continuous non-DC nerve recruitment stimulation pattern (hereinafter referred to as CBAC stimulation) can selectively block the larger afferent A-β fibers (and so reduce or remove the paraesthesia response), while providing activation of smaller diameter fibers sufficient to deliver pain relief by the gate control theory mechanism. In SCS applications this minimizes the paraesthesia sensation while still providing pain reduction. As shown in FIG. 25, the implantable pulse generator 260 is connected to the stimulation lead 262 and presents an electrical waveform that represents the combined CBDC and CBAC waveforms 264 transmitted to the electrode elements. It should be understood by that the different parameters of each waveform, including the frequency and amplitude of each component of this combined waveform, can be independently adjusted, so the final combined waveform can be considered to be a weighted sum of the two or more component waveforms.

Figure 26:
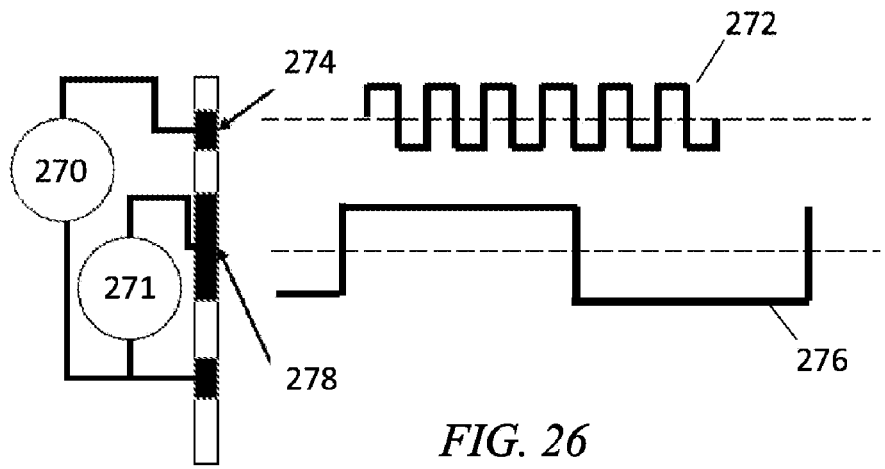
FIG. 26 is a diagrammatic illustration of independently-generated exemplary CBAC waveform and exemplary CBDC waveform for neuro-stimulation according to the teachings of the present disclosure.

FIG. 26 is a diagrammatic illustration of independently-generated exemplary CBAC waveform and exemplary CBDC waveform for neuro-stimulation according to the teachings of the present disclosure. According to another aspect of this disclosure, since electrical fields from different sources combine with the principle of linear superposition, the CBDC and CBAC stimulation patterns can be created by two independent implanted pulse generators 270 and 271 and applied within more than two electrodes (where, for example the CBDC pattern is presented to one electrode and the CBAC pattern to another electrode and a third electrode acts as the return electrode). The first implantable pulse generator 270 generates the CBAC signal 272 which is connected to the electrode 274 on the stimulation lead. The second implantable pulse generator generates the CBDC signal 276 that is connected to the electrode 278 on the stimulation lead. Different parameters of each waveform, including frequency and amplitude of each component waveform can be independently adjusted, so the final field created in the tissue by the resultant combined waveform can be considered to be a weighted sum of the two or more component fields.

Figure 27:
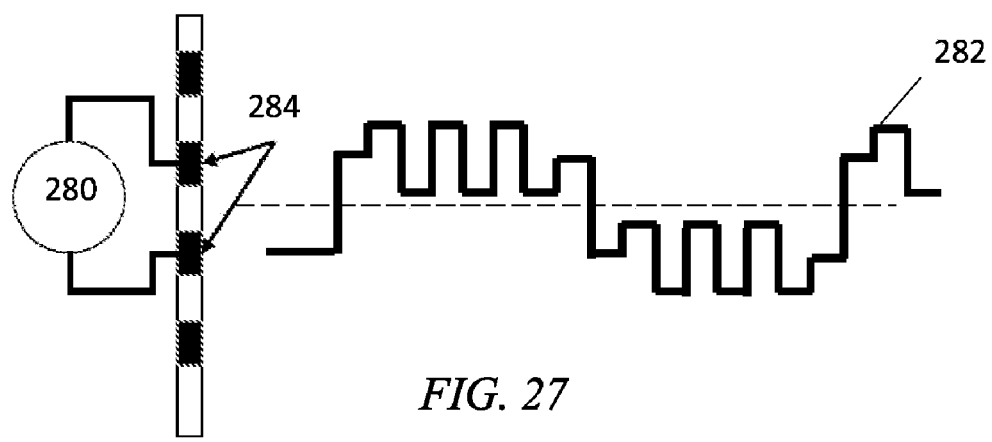
FIG. 27 is a diagrammatic illustration of an exemplary composite waveform that includes a CBAC waveform superimposed onto one phase of a CBDC waveform for neuro-stimulation according to the teachings of the present disclosure.

FIG. 27 is a diagrammatic illustration of an exemplary composite waveform that includes a CBAC waveform superimposed onto one phase of a CBDC waveform for neuro-stimulation according to the teachings of the present disclosure. According to another aspect of this disclosure, the CBAC component of the combined waveform may be continuous or intermittent. The implantable pulse generator 280 presents a signal 282 which is a continuous combination of CBAC and CBDC waveforms to the electrode 284. FIG. 27 shows an example of the intermittent case where the implantable pulse generator 280 presents a signal that has a continuous CBDC component, which is added to an intermittent CBAC component to the electrode 284.

It should be understood by those skilled in the art that there are many ways in which two or more waveforms may be combined continuously and intermittently to achieve the desired effect for neuro-stimulation therapies. Any known or later developed methods to combine two or more waveforms is encompassed herein. Further, the waveform shapes used to create the CBDC and CBAC stimulation patterns may be square, triangular, sinusoidal, or any other symmetric or asymmetric waveform shape.

Nerves in biological organisms typically consist of many neural fibers of varying size. Since the exact shape of the CBAC and CBDC waveforms will affect the diameter of the fibers, the recruit and the block respectively, by varying said CBAC and CBDC waveforms and the way they are combined it is possible to selectively recruit particular diameter fibers in a nerve. In some cases such a selection of particular fibers will promote the production of particular neurotransmitters, selected for specific therapeutic benefit.

Since neuro-stimulation is undertaken to deliver a therapeutic benefit it may be desirable for neuro-stimulators to have some method of determining the extent to which the stimulation being delivered is achieving its intended goal. Such a capability may be beneficial to ensure the patient receives sufficient therapy and to avoid any potential harm or power wastage that may be associated with over delivery of a therapy. The process of automatically measuring some outcome from a neuro-stimulation therapy and using that measurement to control the delivery of either the neuro-stimulation therapy or another therapy is often referred to as "closed-loop stimulation." According to one aspect of this invention neural circuit processing may be used for this and other purposes.

The mechanisms of neuro-stimulation are various and understood to different degrees, depending on the particular therapy in question. One application of peripheral nerve stimulation for pain is to effect a "nerve block" whereby the stimulation is used to effectively block neural transmission, thereby preventing occurrence of action potentials. In other cases, it is understood that neuro-stimulation can promote neural transmission creating action potentials. The result of neural activation is the production of neurotransmitters. A neurotransmitter can be any endogenous chemical that is used to enable neurotransmission, such as GABA (gamma-Aminobutyric acid) or other neurally active agents such as endorphins. It has been shown that occipital nerve stimulation (ONS) stimulates the production of GABA in the Trigeminal Nucleus Caudalis (TNC). It is known that reduced levels of the inhibitory neurotransmitter GABA are linked to migraine severity and frequency of migraine events. The role of neurotransmitters such as GABA is to modify the way neural signals are passed within two or more neurons. The neurotransmitter is released into the synapse (the minute gap at the junction within two nerve cells) by the first neurons and carries the neural impulse to the second neurons by diffusion across the synapse. Different neurotransmitters can modulate the transmission of neural impulses in different ways.

Information about a neural circuit may be derived by comparing the input to the neural circuit with the output of the neural circuit. An example of such a complex neural circuit measurement is the "h reflex" or Hoffman reflex. When electrical stimulation is applied via the stimulation electrode to the input or sensory neurons of a nerve in a muscle, at least two responses may be measured by the measurement electrode in the motor neurons to that nerve. Typically, the sensory neurons and the motor neurons for a muscle are bundled together, so stimulation of sufficient intensity will activate both the sensory neurons in the antidromic direction (towards the spinal cord) and the motor neurons in the orthodromic direction (towards the muscle). The direct activation of motor neurons generates a first response at the measurement electrode called the m-wave, which typically occurs 3-6 msec, after the onset of stimulation. The activation of the sensory neurons activates the reflex arc and generates a second response in the motor neurons called the h-wave, typically 28-35 msec, after stimulation.

Figure 28:
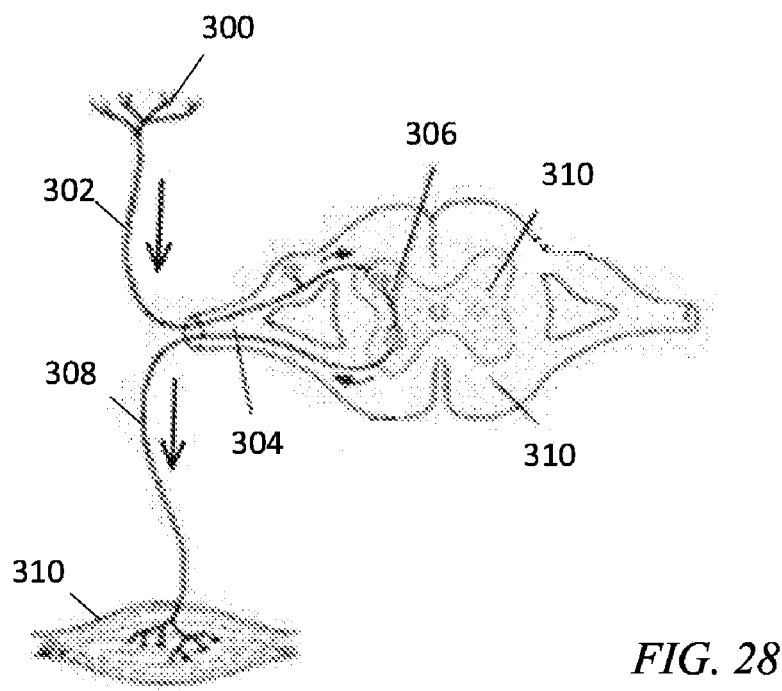
FIG. 28 is a diagrammatic illustration of a neural circuit.

In a neural circuit shown in FIG. 28, the receptor structures 300 of an input neuron detect a trigger input and an electrical signal is transmitted along the input neurons 302 to the spinal cord, via the spinal cord ganglion 304. In the spinal cord the input signal generally follows two pathways. One pathway, not shown in the figure, takes the input signal to the brain, while the other pathway is through the interneuron 306. The input signal triggers the interneurons 306 that in turn triggers an output neuron 308. The output neuron 308, in turn, conveys the signal to an effector, for example a muscle 310. This second pathway, from the receptor 300 via the spinal cord interneurons 306 to the effector 310, is called the reflex arc. The reflex arc allows the body to react quickly to key sensory inputs. It should be understood that in this example, the input (here sensory) and output (here motor) neurons form part of the peripheral neurons system (PNS), while the interneuron in the spinal cord forms part of the central nervous system (CNS).

Peripherally placed neuro-stimulation and recording electrodes may be used to monitor the performance of neural circuits that may include one, two, or more nerve fibers. An example of such a neural circuit is the reflex arc. In the description that follows a reference to a reflex arc shall be understood to refer to any system of interconnected nerve fibers where there are a first neural element that may be considered to be an input to the system (hereinafter referred to as the input neuron); a second neural element that may be considered the output to the neural circuit in question, on whose neural activity may be measured and which synapses to the first element (hereinafter referred to as the output neuron); and possible third or further elements that synapse within the input neuron and the output neuron (hereinafter referred to as the interneuron) and where the behavior of the circuit may be affected by either the stimulation input to the neural circuit or by some other apparatus, for example a drug pump.

Figure 29:
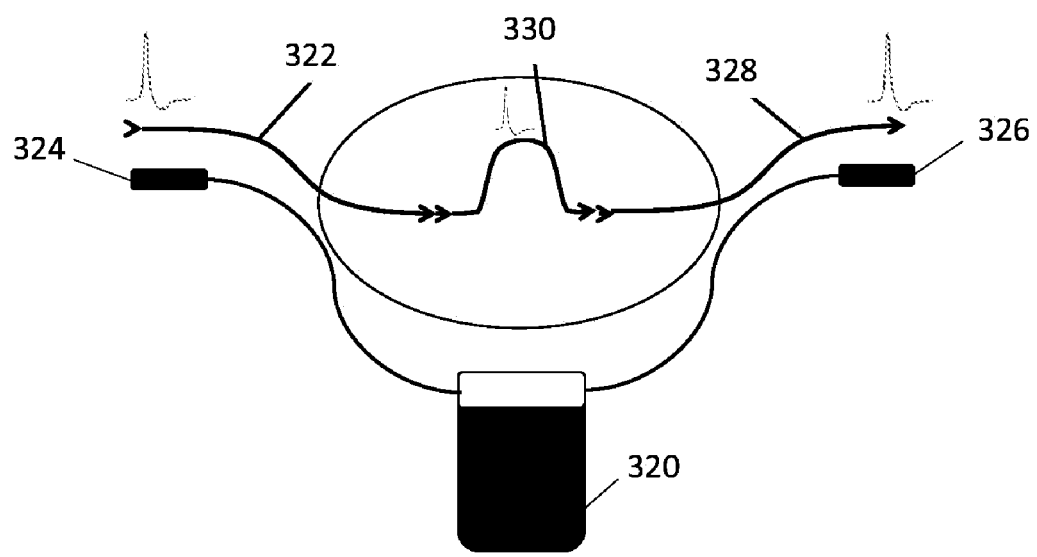
FIG. 29 is a diagrammatic illustration of a representative output signal on the output neurons of a neural arc in response to electrical stimulation of the input neuron of the neural arc according to the teachings of the present disclosure.

FIG. 29 is a diagrammatic illustration of a preferred placement of stimulation and recording electrodes on the neural arc according to the teachings of the present disclosure. An implanted electronics module 320 provides a stimulation pattern to the input neurons 322 via the stimulation electrode 324, and measures the electrical activity on the measurement electrode 326 on the output neuron 328, where the signal traveled from the input neuron 322 to the output neuron 328 via the interneuron 330.

A measurement system and method as is disclosed herein that may be used to monitor the performance of central nervous system neurons that is in the neural circuit. The physical environment of any neuron may have a profound impact on the operation of that neuron. In particular, the operation of various chemicals (collectively called neurotransmitters) to assist or inhibit the transfer of nerve impulses across the synapses within nerves or to assist or inhibit the transmission of impulses along the neuron axon (by, for example, altering the ability of Na and K ions to move across the cell membrane) affects the performance of a neural circuit that contains synapses. An example of such a chemical is Gamma-aminobutyric acid (GABA). This amino acid is the second most prevalent neurotransmitter in the brain and it has an inhibiting effect that calms excited nerve impulses. A deficiency of GABA can cause headaches, depression, irritability, palpitations, and other symptoms. Such a deficiency may be treated by the prescription of other neuro-inhibitors (e.g., tranquilizers in the benzodiazepine family) or dietary supplements of substances that stimulate the body's own production of GABA. Accordingly, the capacity to measure a neural circuit as described herein can be applied to a neural circuit that crosses the CNS. Such a measurement may permit inferences to be drawn about the presence or absence of neurotransmitters such as GABA in the region of the CNS. This methodology may be further extended to the measurement of a wide range of parameters of the neural circuit and permit the drawing of inferences related to many other biological conditions.

It should be understood by those skilled in the art that the capacity to measure a neural circuit as described herein can also be applied to a circuit that involves the autonomic nervous system. As mentioned above, such inferences can be used to understand the effects of stimulation of one point in the autonomic nervous system and its influence on another point of the system. For example, stimulation of the hepatic nerve may activate changes in glucose levels in the blood, the level of glucose detected could allow inferences of the state of the system.

The utility of such measurements includes the detection both permanent and transitory abnormal conditions in the neural circuit being measured; to provide assistance in the manual titration of drugs prescribed to rectify such abnormal conditions; or to provide closed loop control of neuromodulation therapies such as devices designed to deliver such drugs (e.g., implantable drug pumps) or devices which may stimulate the production of such chemicals in the body (e.g., some neuro-stimulation therapies). Since the placement of peripheral electrodes is commonly not very invasive, such electrodes may be implanted for acute trials to determine if a patient is likely to respond to an expensive neuromodulation therapy.

An example of the kind of measurement that might be used to infer information about the neural circuit and its environment is the time between the stimulation of the input neurons to the appearance of a response at the other end of the circuit (i.e., on a output neuron) such as is done in the "h reflex" described earlier. Another example is the threshold level of stimulation required on the input neurons to evoke a response in the other end of the circuit. A third measurement might be to compare the difference in the average power of measured neural activity on the output neurons when stimulation on input neurons is either present, altered, or absent. According to one aspect of this invention neural circuit processing may be used with temporary electrode as a diagnostic aid to allow for particular conditions to be detected and/or quantified.

According to another aspect of this invention neural circuit processing may be used as part of a control loop to ensure or confirm that the desired stimulation paradigm is being appropriately delivered to the sensor nerve.

According to yet another aspect of this invention neural circuit processing may be used as part of a "closed loop" stimulation paradigm to detect particular physiological conditions and customizes therapy delivery to meet that physiological need.

It should be understood that making a measurement such as the h-reflex is critically dependent on the ability to identify the h-wave associated with a particular stimulus. In a clinical setting, when the patient is at rest, this can be readily achieved since circumstances can be arranged to ensure there is little or no other activity on the nerve in question. Out of the clinic, however, it can be expected that normal patient activity will generate activity on the motor neurons that may make it difficult to identify h-wave associated with a stimulus.

To manage this issue, the device measures the relationship within a series of input stimuli and their corresponding output responses. It is understood that if an appropriate input sequence to a system is mathematically correlated with the corresponding output sequence of that system, the cross correlation function will, in many practical situations, have a peak when the two sequences are most closely aligned, even in the presence of other uncorrected output signals.

Figure 30:
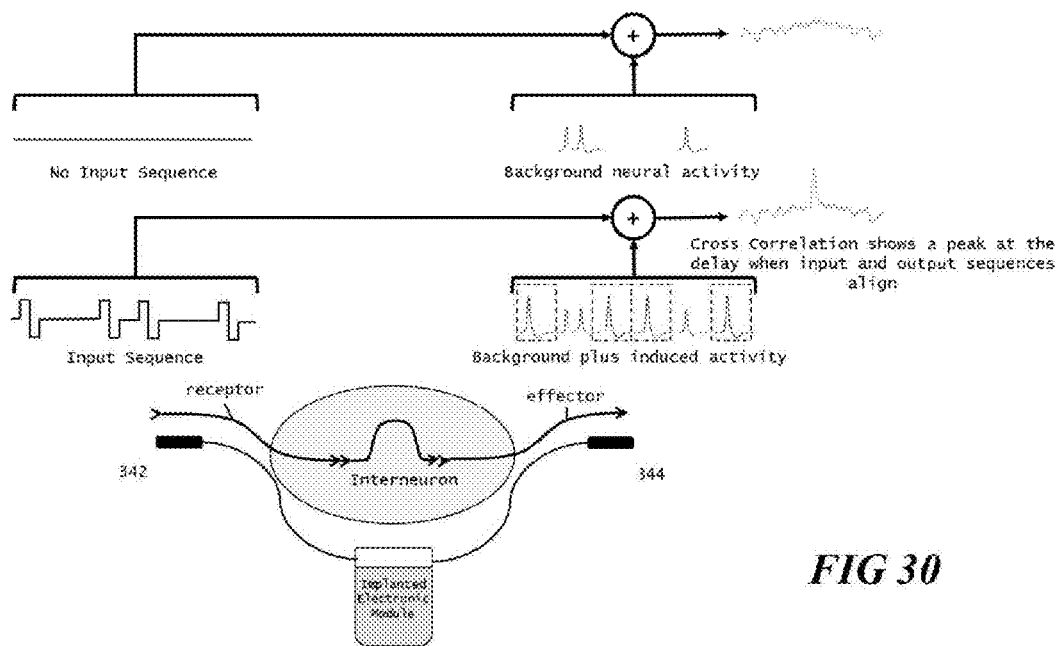
FIG. 30 is a diagrammatic illustration of a representative cross-correlation signal processing technique to reliably measure the influence of the interneurons element according to the teachings of the present disclosure.

FIG. 30 is a diagrammatic illustration of a representative cross-correlation signal processing technique to reliably measure the influence of the interneurons element according to the teachings of the present disclosure. If an input sequence is correlated with itself (its auto-correlation), what is produced is an auto-correlation which has the form of a single "spike" or delta function. If the input sequence is repetitive in nature, then the auto-correlation function shows multiple peaks, spaced equal to the repetition period. If the input sequence has no repetition, then the cross-correlation function will only show multiple peaks if the system under examination introduces multiple responses to each stimulus. An ideal input function is therefore one which closely approximates a "white noise" sequence, though other sequences may also be used. Referring to FIG. 30, an implanted electronics module 340 is configured to stimulate the sensory neurons with a pulse train generated from a pseudo random binary noise (PRBN) generator. The stimulation electrode 342 delivers a pattern of electrical stimulation pulses controlled by the PRBN generator to the sensor neurons. A measurement electrode 344 measures all electrical activity occurring in the output neurons. A signal processing circuitry then cross-correlates the PRBN sequence with the measured activity on the measurement electrode 344. If at least some part of the measured waveform or sequence is due to the PRBN controlled stimulation sequence, then the cross-correlation of these two signals produces a peak at the point where the PRBN sequence is correlated with the neural activity evoked by that sequence. Further, the height of that peak is proportional to the degree of matching within the two sequences and the position of the peak indicates the time delay within the input sequence and the correlated output sequence.

The PRBN generator can be designed with arbitrarily long pseudo-random pulse trains. The need to ensure there is no sequence repetition in the time periods of interest (in general less than 40 msec.) arbitrates in favor of longer sequence lengths, but longer sequences require longer cross-correlation windows to ensure the function is properly computed. In the preferred embodiment, the PRBN sequence length is chosen to appropriately balance these two issues. It should be understood that other stimulation patterns may also have desirable properties and can be used herein as the stimulation waveform.

According to one aspect of this disclosure, the effect that a stimulation pattern applied to the input of a neural circuit has on the average signal power measured on the output of the neural circuit may be used for closed loop control.

Figure 31:
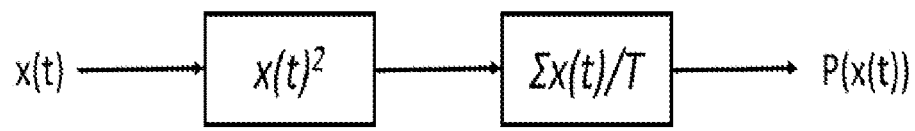
FIG. 31 is a diagrammatic representation of a sum of squares circuit/processor according to the teachings of the present disclosure.

FIG. 31 is a diagrammatic representation of a sum of squares circuit/processor according to the teachings of the present disclosure. The input signal, $x(t)$, is first multiplied by itself ($x(t)2$) and the resulting signal is then summed or integrated over a fixed period ($\Sigma x(t)2/T$). Since the power in a signal is proportional to the square of its amplitude, the resulting output of the integrator stage is proportional to the power in the received signal over the integration period ($P(x(t))$). It should be understood by those skilled in the art that other methods of measuring the power and other properties in a signal are also contemplated herein. For example, the measured output may be transmitted to a computing device that is configured to analyze the output signal and modify or generate a control parameter of the neuro-stimulating device or modifying a parameter or characteristic of the input signal, thus forming a feedback loop.

Figure 32:
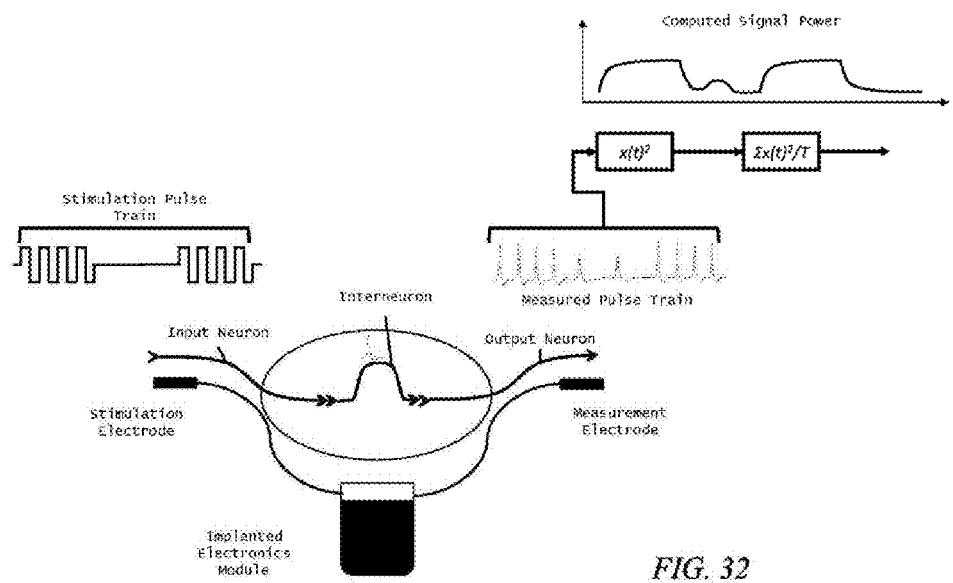
FIG. 32 is a diagrammatic illustration of using a sum or squares signal processing technique to measure the performance of a neural circuit according to the teachings of the present disclosure.

FIG. 32 is a diagrammatic illustration of using a sum or squares signal processing technique to measure the performance of a neural circuit. This method is of particular utility when higher stimulation frequencies are used, but may be used in any situation. The signal measured at the output neurons is a composite of "normal" neural activity (i.e., the signal that is present regardless of any stimulation on the sensor neuron) and activity that is a result of stimulating the sensor neurons. The implanted electronics module is configured to control the higher frequency stimulation signal to be sometimes present and sometimes absent. The measurement electrode detects all the activity on the output neurons, both the naturally occurring activity as well as the activity in response to the stimulation patterns. When the measured signal passes through the sum of squares power detection function, the output of that function is a waveform of which the amplitude is proportional to the power in the measured signal on the output neuron. This measured waveform has some regions where the computed power represents the power in the natural activity of the neurons only (when no stimulation is applied) and other regions where the computed power represents the sum of the natural activity and the activity evoked in the neurons by the stimulation pattern. Over short periods it is very likely to be valid to assume the natural level of neural activity is constant so any difference within the stimulation absent and stimulation present measurements may be interpreted as being due to the applied stimulation. The difference within these two measurements is proportional to both the intensity of the stimulation pattern and the performance of the neural circuit being measured. It may be appreciated by those skilled in the art that this method may also be used to determine the effectiveness of a high frequency stimulation pattern on a neural circuit where no synapse is included.

In many cases, effective neural circuit processing requires information about the performance of the receptor nerve. For example, if the sensitivity of the CNS synapsing functions needs to be estimated, it is desirable to have estimates of the sensor and effector nerves as well. At least the sensitivity of the sensor nerve may be estimated by analyzing the Compound Action Potential (i.e. the sum of individual neural action potentials) evoked by a stimulation pulse. This signal is called the Evoked Compound Action Potential or ECAP. Such information may include threshold stimulation level (the minimum stimulation level at which at least some neurons in the nerve are stimulated), neural conduction velocity (the speed with which the ECAP travels along the nerve) or the spread of individual neural velocities (ECAP shape). Measuring ECAPs is known to be complicated by the presence of the stimulation artefact. This artefact is a result, at least in large part, of capacitance in the stimulation circuit path.

In many cases the effect of the stimulation artifact can be minimized by physically separating the stimulation and measurement electrodes. In some cases, however, this is impractical.

Figure 33:
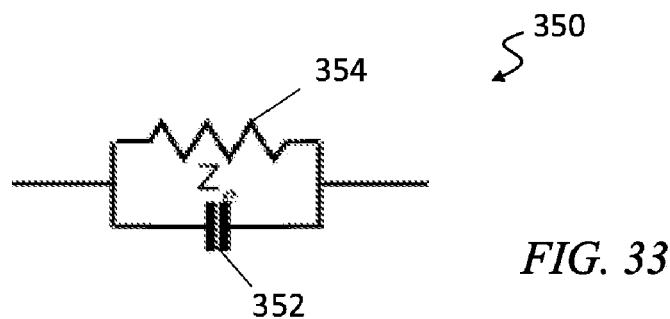
FIG. 33 is a schematic diagram representation of an equivalent circuit 350 of an electrode tissue interface according to the teachings of the present disclosure.

FIG. 33 is a schematic diagram representation of an equivalent circuit 350 of an electrode tissue interface according to the teachings of the present disclosure. The circuit 350 includes a capacitive element 352 coupled in parallel with a resistive element 354. The capacitive element 352 arises from the double layer of ionized electrolyte on the electrode surface.

Figure 34:
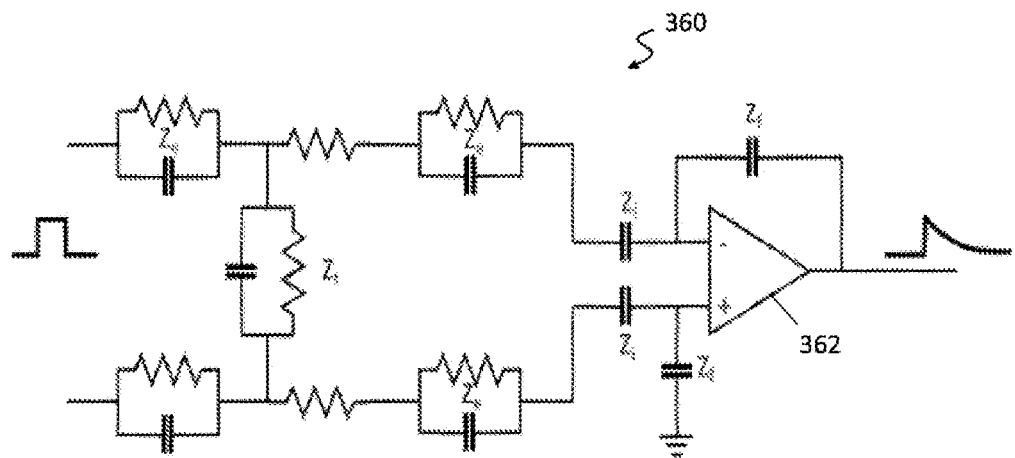
FIG. 34 is a schematic diagram of an equivalent circuit for a stimulation pulse passing through two electrodes with impedance Ze, through the tissue impedance Zt, through two sensing electrodes Z; then into a measurement amplifier according to the teachings of the present disclosure.

FIG. 34 is a schematic diagram of an equivalent circuit 360 for a stimulation pulse passing through two electrodes with impedance Ze, through the tissue impedance Zt, through two sensing electrodes Zi, then into a measurement amplifier 362 according to the teachings of the present disclosure. There are several energy storage elements in the signal path that can give rise to the electrode artifact shown at the output of the amplifier 362. When the stimulation level generates a field that exceeds the activation function of the nerve being stimulated, then the signal at the output of the measurement amplifier 362 is the sum of the artifact, the Evoked Compound Action Potential (ECAP), and any other electrical noise. For any practical stimulation signal, the artifact may have an amplitude of tens to thousands of milli-volts compared to the ECAP signal of micro-volts or tens of micro-volts. An amplifier capable of measuring the ECAP without being overloaded by the artifact would need a dynamic range in the order of 120 dB, for example. Since this is hard to achieve in a device suitable for implantation, the measurement amplifier has a time-varying gain such that the gain of the amplifier increases over time, inversely with the expected level of the artifact. In this way, the measurement amplifier does not overload, and the true value of the measurement signal can be digitally reconstructed by multiplying the measured signal with the gain function. In many cases the artifact signal is either effectively constant or can be modeled as a function of a small number of parameters. These parameters may include stimulation voltage or current, stimulation duration, and other parameters. The measurement device has the capacity to generate an artifact model based on suitable input parameters and to appropriately combine this model with the measurement signal to generate a good estimate of the ECAP signal.

Where it is desirable to estimate the amplitude of the ECAP signal there are several methods known in the art that may be applied. Methods which are computationally efficient, such as simple amplitude detection, are often susceptible to noise. More sophisticated methods such as matched filters, correlation techniques methods and even wavelet processing techniques are less susceptible to corruption by noise, but in every case these methods can sometimes produce an estimate of an ECAP, even when one is not present. Where this estimate is used by a control algorithm such behavior will cause the algorithm to behave unpredictably.

Figure 35:
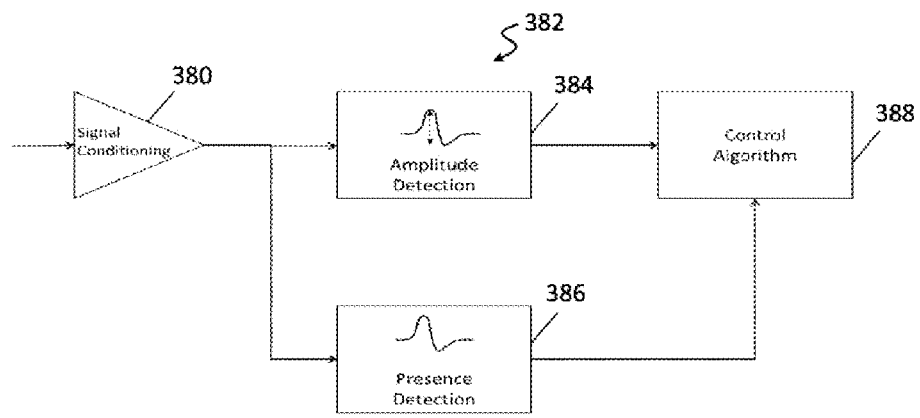
FIG. 35 is a block diagram of a system for enhancing detection performance with a signal present estimator according to the teachings of the present disclosure.
Figure 36:
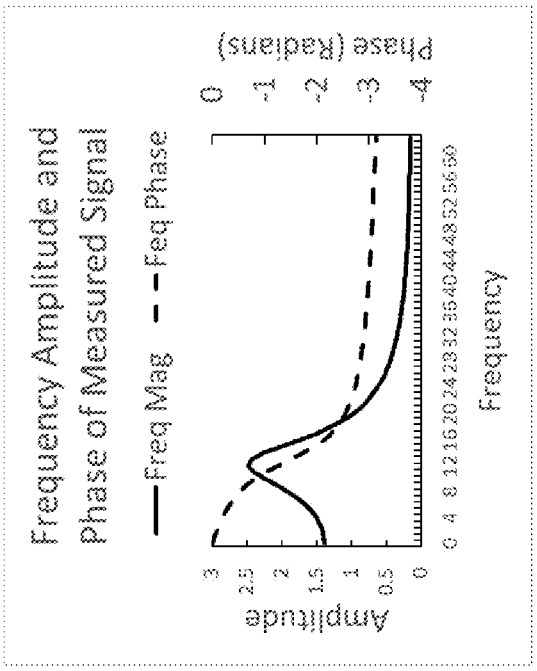
Figure 37:
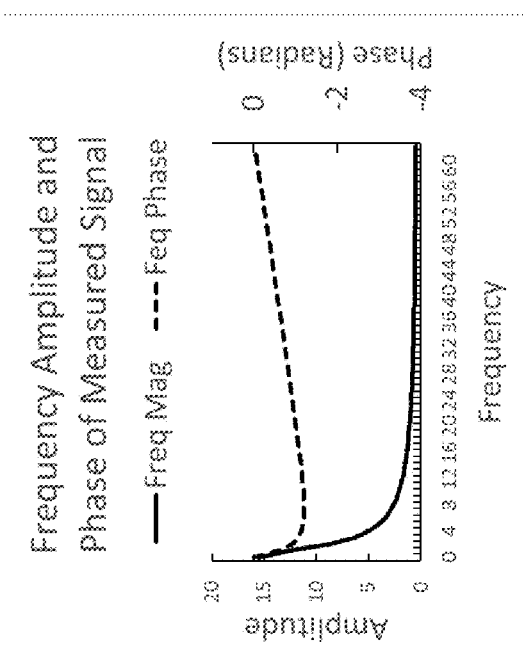
Figure 38:
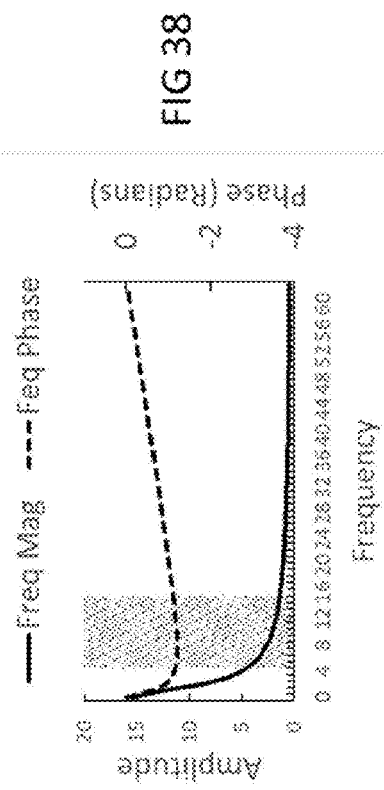
Figure 39:
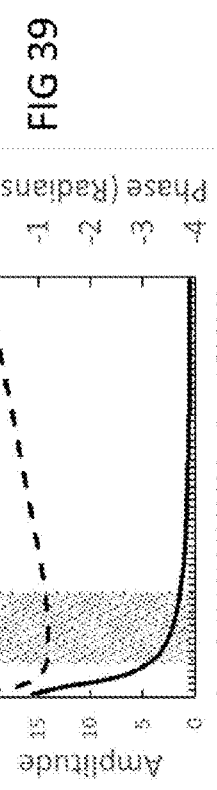

FIG. 35 is a block diagram of a system for enhancing detection performance with a signal present estimator according to the teachings of the present disclosure. The amplitude detection algorithm is managed or "gated" by a separate algorithm used to estimate the presence or absence of an ECAP in the measured signal. In this apparatus, the signal is passed through a conditioning stage 380 that may provide, for example, low input capacitance, level shifting, amplification or other suitable condition steps. The signal is then presented to a "signal detection" device 382 that includes an amplitude detecting element 384 that estimates the power in the signal, and a "presence detection" element 386 that is configured to recognize the presence of the desired signal. The output of both these elements 384 and 386 is then passed to the control unit 388. The control unit 388 applies a suitable control strategy when reliable signal measurement can be made, and a potentially different control strategy when no reliable measurement can be made. It should be understood by those skilled in the art that this structure allows for each detection algorithm to be optimized for their particular purpose and improves the overall performance of the control algorithm. When the "presence detector" 386 estimates that no signal is present, the control algorithm can ignore the amplitude or power estimate from the amplitude detecting element 384 and behave according to predefined rules to ensure the safety and efficacy of the device.

According to another aspect of this disclosure, one method for detecting ECAP presence is achieved by examining the phase behavior of the Fourier transform of the measured signal. FIGS. 36-43 are amplitude and phase spectra of estimates of ECAP and Artifact signals according to the teachings of the present disclosure.

The features of the present invention which are believed to be novel are set forth below with particularity in the appended claims. However, modifications, variations, and changes to the exemplary embodiments described above will be apparent to those skilled in the art, and the system and method described herein thus encompass such modifications, variations, and changes and are not limited to the specific embodiments described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An implantable electrical stimulation device comprising:
   a porous substrate constructed of a bio-compatible and bio-survivable material; and
   at least one electrically conductive electrode embedded in the porous substrate and configured for coupling with a pulse generator device and for transmitting an electrical signal from the generator device to generate an electric field around a target tissue, wherein the porous substrate is configured to fully support the at least one electrically conductive electrode to provide structural integrity to the implantable electrical stimulation device;
   wherein the porous substrate is characterized by at least one of the following properties:
   (a) the porous substrate mimics extracellular matrix;
   (b) the porous substrate has a pore size selected to control tissue ingrowth;
   (c) the porous substrate is constructed of non-woven fibers; and
   (d) the porous substrate is substantially free from structural element disposed therein.

2. The implantable electrical stimulation device of claim 1, wherein the porous substrate has a pore size is selected to allow only superficial cellular ingrowth.

3. The implantable electrical stimulation device of claim 1, wherein the porous substrate has a pore size is selected to allow only cellular ingrowth in selected areas the substrate.

4. The implantable electrical stimulation device of claim 1, wherein the porous substrate has a pore size is in the range from 2 μm to 10 μm.

5. The implantable electrical stimulation device of claim 1, wherein the porous substrate is constructed of non-woven fibers and the non-woven fibers are polymeric fibers.

6. The implantable electrical stimulation device of claim 5, wherein the polymeric fibers are selected from a group consisting of polyurethane (thermoplastic and thermoset), polyethylene terephthalate, polyether ether ketone, polytetrafluoroethylene and poly-methyl-methacrylate.

7. The implantable electrical stimulation device of claim 1 wherein the porous substrate supports the one or more conductive electrodes in such a way that part of one or more electrodes and the surrounding porous substrate can be removed without compromising the integrity of the overall structure.

8. The implantable electrical stimulation device of claim 1, further comprising at least one intermediate non-porous layer disposed on or within the porous substrate.

9. The implantable electrical stimulation device of claim 1, further comprising an electrically conductive field shaping element embedded within the porous substrate and configured for shaping the electric field generated by the electrically conductive electrode.

10. The implantable electrical stimulation device of claim 1, further comprising an electrically insulated lead embedded within the porous substrate and configured for shaping the electric field generated by the electrically conductive electrode.

11. The implantable electrical stimulation device of claim 1, further comprising an electrically conductive inclusion configured to function as an electrical connecting element disposed within or on the porous substrate.

12. The implantable electrical stimulation device of claim 1, further comprising a biocompatible inclusion in the form of barbed structures configured to function as an anchor structure at least partly disposed within the porous substrate.

13. The implantable electrical stimulation device of claim 1, wherein a pore size of at least one region of at least one of the porous substrate is different than a pore size in another region of the porous substrate.

14. The implantable electrical stimulation device of claim 1, wherein the lead assembly is in the form and structure of one of a patch lead, paddle lead, cuff lead, helical lead, transvenous lead, conformal lead and catheter lead.

15. The implantable electrical stimulation device of claim 1, wherein the lead assembly is configured for generating an electric field around a target nerve.

16. An implantable electrical stimulation device comprising:
   a porous substrate constructed of a bio-compatible and bio-survivable material; and
   at least one electrically conductive electrode embedded in the porous substrate and configured for coupling with a pulse generator device and for transmitting an electrical signal from the generator device to generate an electric field around a target tissue, wherein the porous substrate is configured to fully support the at least one electrically conductive electrode to provide structural integrity to the implantable electrical stimulation device;
   wherein the porous substrate comprises two or more materials, at least one of which is selected to facilitate bonding with another part of the membrane or another membrane by the application of heat, pressure, bonding agent or other means.

17. An implantable electrical stimulation device comprising:
   a porous substrate constructed of a bio-compatible and bio-survivable material; and
   at least one electrically conductive electrode embedded in the porous substrate and configured for coupling with a pulse generator device and for transmitting an electrical signal from the generator device to generate an electric field around a target tissue, wherein the porous substrate is configured to fully support the at least one electrically conductive electrode to provide structural integrity to the implantable electrical stimulation device;
   further comprising at least one of the following:
   (a) at least one electrically non-conductive inclusion that is impervious to electrolyte penetration disposed on or within the porous substrate;
   (b) a biocompatible and resorbable inclusion configured to function as a structural element disposed within the porous substrate;
   (c) further comprising a biocompatible inclusion configured to function as an anchor structure at least partly disposed within the porous substrate;
   (d) a second porous substrate constructed around at least some of the lead structure to allow retraction and removal of the lead structure post-implantation.

18. An implantable electrical stimulation device comprising:
   a porous substrate constructed of a bio-compatible and bio-survivable material; and
   at least one electrically conductive electrode embedded in the porous substrate and configured for coupling with a pulse generator device and for transmitting an electrical signal from the generator device to generate an electric field around a target tissue, wherein the porous substrate is configured to fully support the at least one electrically conductive electrode to provide structural integrity to the implantable electrical stimulation device;

wherein at least one selected region of the porous substrate is (a) impervious to electrolyte penetration, (b) coated with an electrically non-conductive material for the purpose of shaping the electric field, or (c) coated with an electrically non-conductive material for the purpose of modifying surface properties of the lead assembly.

19. An implantable electrical stimulation device comprising:

a porous substrate constructed of a bio-compatible and bio-survivable material; and at least one electrically conductive electrode embedded in the porous substrate and configured for coupling with a pulse generator device and for transmitting an electrical signal from the generator device to generate an electric field around a target tissue, wherein the porous substrate is configured to fully support the at least one electrically conductive electrode to provide structural integrity to the implantable electrical stimulation device;

further comprising a pulse generator circuit embedded within the porous substrate and electrically connected to the at least one electrically conductive electrode, wherein the pulse generator circuit further includes an inductive coil configured to be energized by energy transmitted by an energy source that is external to the body.

20. The implantable electrical stimulation device of claim 19, wherein the pulse generator circuit further includes a power supply.

21. The implantable electrical stimulation device of claim 19, wherein the external energy source is incorporated in a wearable accessory selected from the group consisting of a hat, a headband, a necklace, eyeglasses, sports headphone-like structure, a purse, a collar, and a Velcro patch.

* * * * *